US012362596B2

(12) United States Patent
Barker et al.

(10) Patent No.: US 12,362,596 B2
(45) Date of Patent: Jul. 15, 2025

(54) WEARABLE PHYSIOLOGICAL MONITORING DEVICES

(71) Applicant: Masimo Corporation, Irvine, CA (US)

(72) Inventors: Nicholas Evan Barker, Laguna Beach, CA (US); Bilal Muhsin, Irvine, CA (US); Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 344 days.

(21) Appl. No.: 17/820,485

(22) Filed: Aug. 17, 2022

(65) Prior Publication Data

US 2023/0147750 A1    May 11, 2023

Related U.S. Application Data

(60) Provisional application No. 63/235,008, filed on Aug. 19, 2021, provisional application No. 63/235,412, (Continued)

(51) Int. Cl.
*H02J 50/10* (2016.01)
*A61B 5/00* (2006.01)
(Continued)

(52) U.S. Cl.
CPC .......... *H02J 50/10* (2016.02); *A61B 5/02438* (2013.01); *A61B 5/11* (2013.01); *A61B 5/681* (2013.01); *H02J 7/0013* (2013.01); *H02J 7/342* (2020.01); *A61B 5/742* (2013.01); *A61B 5/746* (2013.01); *A61B 2560/0219* (2013.01); *H02J 7/0042* (2013.01)

(58) Field of Classification Search
None
See application file for complete search history.

(56) References Cited

U.S. PATENT DOCUMENTS 4,960,128 A    10/1990    Gordon et al.
4,964,408 A    10/1990    Hink et al.
(Continued)

OTHER PUBLICATIONS

US 2024/0016391 A1, 01/2024, Lapotko et al. (withdrawn)

*Primary Examiner* — Carl H Layno
*Assistant Examiner* — Manolis Pahakis
(74) *Attorney, Agent, or Firm* — Knobbe, Martens, Olson & Bear, LLP

(57) ABSTRACT

A wearable device including at least one sensor configured to sense a physiological parameter of a user. The wearable device including a base housing and a removable housing attachable to the base housing. The base housing and the removable housing portions each including a battery and an electronic subsystem in communication with each other. The battery of the removable housing portion charges the battery of the base housing portion when the removable housing portion is attached to the base housing portion. A second embodiment includes two or more fitness trackers each having an enclosure. The enclosures of the two or more fitness trackers having complimentary shapes that form a unified enclosure when the enclosures are placed adjacently. In a third embodiment, a wearable device includes a first screen display and a second screen display. The second screen display is transparent in at least one operational mode of the wearable device.

5 Claims, 28 Drawing Sheets

Related U.S. Application Data filed on Aug. 20, 2021, provisional application No. 63/234,983, filed on Aug. 19, 2021.

(51) Int. Cl.
    *A61B 5/024*     (2006.01)
    *A61B 5/11*     (2006.01)
    *H02J 7/00*     (2006.01)
    *H02J 7/34*     (2006.01)

(56) References Cited

U.S. PATENT DOCUMENTS

| | | |
|---|---|---|
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,828,966 A * | 10/1998 | Davis .................. H01M 50/247 379/446 |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |

(56) References Cited

U.S. PATENT DOCUMENTS

| | | |
|---|---|---|
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,331,731 B2 * | 5/2016 | Wang .................... H04B 1/385 |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |

(56) References Cited

U.S. PATENT DOCUMENTS

| | | |
|---|---|---|
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| 10,139,859 B2 * | 11/2018 | von Badinski ......... G06F 21/32 |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,498,158 B2 * | 12/2019 | Chen .................... A44C 5/0007 |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,599,101 B2 * | 3/2020 | Rothkopf ............. G04G 21/025 |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,973,424 B2 * | 4/2021 | Lee .................. H01M 10/0431 |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,156,965 B1 * | 10/2021 | Trapero Martin ..... A61B 5/681 |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |

(56) References Cited

U.S. PATENT DOCUMENTS

| | | |
|---|---|---|
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen et al. |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0055928 A1* | 3/2010 | Randall ............... H02J 50/10 439/534 |
| 2010/0060230 A1* | 3/2010 | Schein ................ H02J 7/342 320/103 |
| 2010/0099964 A1 | 4/2010 | O'Reilly et al. |
| 2010/0109890 A1* | 5/2010 | Montplaisir ........... H02J 7/342 320/162 |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0148352 A1* | 6/2011 | Wang ................. B60R 11/0241 320/108 |
| 2011/0172498 A1 | 7/2011 | Olsen et al. |
| 2012/0123231 A1 | 5/2012 | O'Reilly |
| 2012/0165629 A1 | 6/2012 | Merritt et al. |
| 2012/0176087 A1* | 7/2012 | Lee ..................... H01R 24/62 439/345 |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0137731 A1* | 5/2015 | Kim ..................... H02J 7/342 361/679.01 |
| 2015/0340891 A1* | 11/2015 | Fish .................... H02J 7/342 320/103 |
| 2016/0091922 A1* | 3/2016 | Nazzaro .............. G04C 10/00 307/104 |
| 2016/0268826 A1* | 9/2016 | Chiba ................. H02J 7/0042 |
| 2017/0024748 A1 | 1/2017 | Haider |
| 2017/0135315 A1* | 5/2017 | Marmen ............. A01K 15/021 |
| 2017/0173632 A1 | 6/2017 | Al-Ali |
| 2017/0251974 A1 | 9/2017 | Shreim et al. |
| 2017/0277138 A1* | 9/2017 | Kaji .................... G06F 3/03547 |
| 2018/0153317 A1* | 6/2018 | Haroush .............. A47F 7/024 |

(56) References Cited

U.S. PATENT DOCUMENTS

| | | |
|---|---|---|
| 2018/0242926 A1 | 8/2018 | Muhsin et al. |
| 2018/0247712 A1 | 8/2018 | Muhsin et al. |
| 2018/0259914 A1* | 9/2018 | Chae .................. G04G 19/00 |
| 2019/0239787 A1 | 8/2019 | Pauley et al. |
| 2019/0320906 A1 | 10/2019 | Olsen |
| 2020/0060869 A1 | 2/2020 | Telfort et al. |
| 2020/0073337 A1* | 3/2020 | Wang .................. G06F 1/1656 |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329983 A1 | 10/2020 | Al-Ali et al. |
| 2020/0329993 A1 | 10/2020 | Al-Ali et al. |
| 2020/0343745 A1* | 10/2020 | Choi .................. H02J 7/0044 |
| 2020/0350774 A1* | 11/2020 | Kim .................. G04G 17/08 |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0126477 A1* | 4/2021 | DeMaio .............. H01M 50/247 |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0117558 A1* | 4/2022 | Nicolae .............. A61B 5/02405 |
| 2022/0151207 A1* | 5/2022 | Mott .................. A01K 29/005 |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0357780 A1* | 11/2022 | Bhagwan .............. G06F 1/263 |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2022/0395225 A1* | 12/2022 | Schena .............. A61B 5/02416 |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0081378 A1* | 3/2023 | Steinberg .............. A61B 5/681 |
| | | 320/109 |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0198298 A1* | 6/2023 | Lee .................. H02J 7/342 |
| | | 307/104 |
| 2023/0210417 A1* | 7/2023 | Al-Ali .................. A61B 5/6826 |
| | | 600/323 |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0361588 A1* | 11/2023 | Sanchez .............. H02J 50/001 |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0128772 A1* | 4/2024 | Kuipers .............. H02J 7/0042 |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0322579 A1* | 9/2024 | Nodet .................. G04G 19/00 |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |

* cited by examiner

WEARABLE PHYSIOLOGICAL MONITORING DEVICES

INCORPORATION BY REFERENCE TO ANY PRIORITY APPLICATIONS

The present application claims priority to U.S. Provisional Application No. 63/235,412, filed Aug. 20, 2021, U.S. Provisional Application No. 63/234,983, filed Aug. 19, 2021, and U.S. Provisional Application No. 63/235,008, filed Aug. 19, 2021. All of the above-listed applications and any and all other applications for which a foreign or domestic priority claim is identified in the Application Data Sheet as filed with the present application, are hereby incorporated by reference under 37 CFR 1.57.

FIELD OF THE DISCLOSED EMBODIMENTS

The subject matter of the present application is in the field of wearable devices having at least one sensor for sensing a physiological parameter of a user.

BACKGROUND OF THE DISCLOSED EMBODIMENTS

Wearable devices, including smartwatches, rings, auricular devices, glasses, can provide multiple functions. In addition to providing conventional time and calendar functions, smartwatches also provide an interface to a smartphone to enable a user to communicate via the smartphone without having to hold the smartphone. A smartwatch can include a 3-axis accelerometer to detect motion and orientation of the user to thereby monitor the user's steps and other actions. A smartwatch may also detect physiological parameters of the user via one or more sensory interfaces on a surface of the smartwatch adjacent to a portion of a user's limb (e.g., the user's wrist). For example, a smartwatch can include an optical heart rate sensor to detect the user's heartrate, an $SpO_2$ monitor to measure blood oxygen levels, a bioimpedance sensor to measure respiratory rate, heart rate, water level and the like.

SUMMARY

A need exists for a way to charge a smartwatch without losing the ability to monitor the user's physiological parameters while the smartwatch is charging. A need also exists for a fitness tracker that has only single or a small set of functionality that can be chosen by a user. If additional functionality is desired by a user, one or more additional fitness trackers can be chosen by the user and placed on a wrist or ankle adjacent to a first fitness tracker. A need also exists for a fitness tracker that is configured to be decorative which can include aesthetically pleasing and less bulky than conventional smartwatches. For wearable devices capable of providing multiple functionalities, there is a need for some functionalities to be displayed more frequently than other functionalities. For example, it may be beneficial for a smartwatch to continually display the time of day and/or date so that a user may view the time of day and/or date without performing an action to cause the smartwatch to display the time of day. It may also be beneficial to display certain parameters in an always on display. For example, step counts may be always displayed.

In one aspect, a wearable device for monitoring one or more physiological parameters of a user can comprise a base housing portion configured for placement on a portion of the user's body, the base housing portion having at least one sensor for sensing a physiological parameter when the wearable device is in use, wherein the base housing portion does not include a display; a first electronic subsystem within the base housing portion configured to process one or more signals generated by the at least one sensor and to generate a wireless communication signal based on the sensed signals; a first battery within the base housing portion and configured to provide power to the first electronic subsystem; a removable housing portion comprising a display and attachable to a top surface of the base housing portion; and a second electronic subsystem within the removable housing portion, the second electronic subsystem powered by a second battery, the second battery selectively couplable to an external charger when the removable housing portion is removed from the base housing portion, wherein, when the removable housing portion is attached to the base housing portion, the second battery within the removable housing portion is configured to charge the first battery within the base housing portion.

The wearable device of any of the preceding paragraphs and/or any of the apparatuses, systems, or devices disclosed herein can include one or more of the following features. In some cases, the display of the removable housing portion can occupy an entire top surface of the removable housing portion. In some cases, the display of the removable housing portion can display a dynamic hour hand and a dynamic minute hand, the dynamic hour hand and the dynamic minute hand can provide an indication to the user of time. In some cases, the display of the removable housing portion can display at least one numerical value indicative of a physiological parameter of the user. In some cases, the base housing portion can further include a first slot comprising a first opening and a second opening smaller than the first opening; and a second slot comprising a first opening and a second opening smaller than the first opening. In some cases, the removable housing portion can further include a first engagement post including a first end and a second end, wherein the first end can be larger than the second end; and a second engagement post including a first end and a second end, wherein the first end can be larger than the second end. In some cases, the first and second slots of the base housing portion can receive the first and second engagement posts of the removable housing portion when the removable housing portion is attached to the base housing portion. In some cases, the first openings of the first and second slots can receive the first ends of the first and second engagement posts when the removable housing portion is attached to the base housing portion. In some cases, the second openings of the first and second slots can receive the second ends of the first and second engagement posts when the removable housing portion is attached to the base housing portion and rotated along a surface of the base housing portion. In some cases, the wearable device can further include a band including a first end and a second end. In some cases, the first end of the band can be attached to a first end of the base housing portion and the second end of the band can be attached to a second end of the base housing portion. In some cases, the base housing portion can wirelessly communicate with the removable housing portion. In some cases, the second electronic subsystem can receive and process the wireless communication signal generated by the first electronic subsystem.

In another aspects, a method of charging a wearable device can include detaching a removable housing portion of the wearable device from a base housing portion of the wearable device, the removable housing portion enclosing a main battery therein, the base housing portion enclosing an auxiliary battery therein; positioning the removable housing portion of the wearable device on a charging source to charge the main battery; maintaining the base housing portion in sensory communication with a user while the removable housing portion is detached, the base housing portion receiving power from the auxiliary battery; reattaching the removable housing portion to the base housing portion after charging the main battery; and charging the auxiliary battery with energy from the main battery when the removable housing portion is attached to the base housing portion.

The method of any of the preceding paragraphs herein can include one or more of the following steps and/or features. In some cases, the base housing portion can wirelessly communicate with the removable housing portion while the removable housing portion is removed from the base housing portion. In some cases, detaching the removable housing portion of the wearable device from the base housing portion of the wearable device can include rotating the removable housing portion about a surface of the base housing portion and removing a first engagement post and a second engagement post of the removable housing portion from a first slot and a second slot of the base housing portion. In some cases, reattaching the removable housing portion to the base housing portion after charging the main battery can include inserting a first engagement post and a second engagement post of the removable housing portion to a first slot and a second slot of the base housing portion and rotating the removable housing portion along a surface of the base housing portion. In some cases, maintaining the base housing portion in sensory communication with the user while the removable housing portion is detached can include securing a band to a portion of the user's body, the band attached to a first end and a second end of the base housing portion. In some cases, the method can include using at least one sensor of the wearable device to sense a physiological parameter of the user when the wearable device is in use.

In another aspects, a wearable device for monitoring one or more physiological parameters of a user can include a main body for placement on a user's limb, the main body including a display and a first input electrode and a second input electrode positioned on a bottom surface of the main body; a first battery inside the main body; and a removable housing comprising a second battery, a top surface, and an opening along the top surface, said removable housing attachable to a top surface of the main body, the removable housing including a plurality of attachment legs configured to engage to the main body to removably secure the removable housing to the main body, the removable housing including at least a first output electrode positioned on an inner surface of a first attachment leg of the plurality of attachment legs and a second output electrode positioned on an inner surface of a second attachment leg of the plurality of attachment legs, the first output electrode positioned on the first attachment leg such that the first output electrode contacts the first input electrode when the removable housing is secured to the main body and such that the second output electrode on the second attachment leg contacts the second input electrode when the removable housing is secured to the main body, wherein, when the removable housing is attached to the main body, the second battery of the removable housing can charge the first battery within the main body via the first and second input electrodes and the first and second output electrodes; and wherein the opening along the top surface of the removable housing can permit visualization of the display of the main body when the removable housing is attached to the main body.

The wearable device of any of the preceding paragraphs and/or any of the apparatuses, systems, or devices disclosed herein can include one or more of the following features. In some cases, the removable housing portion does not include a display. In some cases, the wearable device can include a band including a first end and a second end, wherein the first end attaches to a first end of the main body and the second end attaches to a second end of the main body. In some cases, the main body can include a third input electrode and a fourth input electrode positioned on the bottom surface of the main body; the removable housing can include a third output electrode positioned on an inner surface of a third attachment leg of the plurality of attachment legs and a fourth output electrode positioned on an inner surface of a fourth attachment leg of the plurality of attachment legs; and the third output electrode can contact the third input electrode and the fourth output electrode can contact the fourth input electrode when the removable housing is secured to the main body. In some cases, the main body can include at least one sensor for sensing a physiological parameter of the user when the wearable device is in use.

In another aspects, a method of charging a wearable device while the wearable device is being worn by a user can include attaching a charged removable battery pack to a main body of the wearable device by positioning a plurality of engagement surfaces against respective portions of the main body of the wearable device; engaging a first output electrode of the removable battery pack with a first input electrode of the main body of the wearable device to provide a first electrical contact between the first output electrode and the first input electrode; engaging a second output electrode of the removable battery pack with a second input electrode of the main body of the wearable device to provide a second electrical contact between the second output electrode and the second input electrode; and charging a battery within the main body of the wearable device with power from a battery within the removable battery pack by propagating electrical energy via the first electrical contact and the second electrical contact.

The method of any of the preceding paragraphs herein can include one or more of the following steps and/or features. In some cases, the first output electrode can be positioned on a first engagement surface of the plurality of engagement surfaces and the second output electrode can be positioned on a second engagement surface of the plurality of engagement surfaces. In some cases, the method can include engaging a third output electrode of the removable battery pack with a third input electrode of the main body of the wearable device to provide a third electrical contact between the third output electrode and the third input electrode; and engaging a fourth output electrode of the removable battery pack with a fourth input electrode of the main body of the wearable device to provide a fourth electrical contact between the fourth output electrode and the fourth input electrode. In some cases, the first output electrode can be positioned on a first engagement surface of the plurality of engagement surfaces; the second output electrode can be positioned on a second engagement surface of the plurality of engagement surfaces; the third output electrode can be positioned on a third engagement surface of the plurality of engagement surfaces; and the fourth output electrode can be positioned on a fourth engagement surface of the plurality of engagement surfaces. In some cases, attaching the charged removable battery pack to the main body of the wearable device by positioning the plurality of engagement surfaces against respective portions of the main body can include attaching a plurality of legs against respective portions of the main body. In some cases, the method can include securing a band to a portion of the user's body, the band attached to a first end and a second end of the base housing portion. In some cases, the method can include using a sensor of the main body to sense at least one physiological parameter of the user when the wearable device is in use.

In another aspects, a system of at least a first fitness tracker and a second fitness tracker, each fitness tracker capable of wirelessly communicating a respective physiological parameter of a user to a remote device can include a first enclosure of the first fitness tracker, the first enclosure including a first electronic subsystem comprising at least one sensor configured to sense a first physiological parameter of the user when the first fitness tracker is in use, the first electronic subsystem can wirelessly transmit signals to the remote device responsive to the first physiological parameter, the first enclosure couplable to a first band configured to attach to a portion of the user's body; and a second enclosure of the second fitness tracker, the second enclosure including a second electronic subsystem including at least one sensor configured to sense a second physiological parameter of the user when the second fitness tracker is in use, the second electronic subsystem can wirelessly transmit signals to the remote device responsive to the second physiological parameter, the second enclosure couplable to a second band configured to attach to a portion of the user's body; and wherein the first enclosure includes at least a first engagement surface, the first engagement surface having at least a first selected contour; and wherein the second enclosure includes at least a second engagement surface, the second engagement surface having at least a second selected contour, the second selected contour selected with respect to the first selected contour such that the second engagement surface of the second enclosure interlocks with the first engagement surface of the first enclosure.

The system of at least a first fitness tracker and a second fitness tracker of any of the preceding paragraphs and/or any of the apparatuses, systems, or devices disclosed herein can include one or more of the following features. In some cases, the portion of the user's body can include a limb. In some cases, the first band can include a first magnet and a second magnet; the second band can include a third magnet and a fourth magnet; the first and third magnets can have opposing poles, the first and third magnets can attach to each other and secure at least a portion of the first band to at least a portion of the second band; and the second and fourth magnets can have opposing poles, the second and fourth magnets can attach to each other and secure at least a portion of the first band to at least a portion of the third band. In some cases, the first band can include a fifth magnet and a sixth magnet; the second band includes a seventh magnet and an eighth magnet; the fifth and seventh magnets can have opposing poles, the fifth and seventh magnets can attach to each other and secure at least a portion of the first band to at least a portion of the second band; and the sixth and eighth magnets can have opposing poles, the second and fourth magnets can attach to each other and secure at least one portion of the first band to at least one portion of the third band. In some cases, the at least one first selected contour and the at least one second selected contour can be the same. In some cases, the first physiological parameter can be motion of the user. In some cases, the second physiological parameter can be a heartrate of the user. In some cases, the first physiological parameter can be a heartrate of the user. In some cases, the system includes a third fitness tracker positioned between the first fitness tracker and the second fitness tracker, the third fitness tracker including a third enclosure including a third electronic subsystem including at least one sensor configured to sense a third physiological parameter of the user when the third fitness tracker is in use, the third electronic subsystem can wirelessly transmit signals to the remote device responsive to the third physiological parameter, the third enclosure couplable to a third band that can attach to a portion of the user's body; and the third enclosure including at least a third engagement surface and a fourth engagement surface, the third engagement surface including at least a third selected contour, the third selected contour selected with respect to the first selected contour such that the third engagement surface of the third enclosure can interlock with the first engagement surface of the first enclosure, the fourth engagement surface having at least a fourth selected contour, the fourth selected contour selected with respect to the second selected contour such that the fourth engagement surface of the third enclosure can interlock with the second engagement surface of the second enclosure. In some cases, the first, second, and third physiological parameters can be different from each other. In some cases, the wirelessly transmitted signal of the first and second electronic subsystems can include an alert. In some cases, the wirelessly transmitted signal of the first and second electronic subsystems can be received and processed by the remote device. In some cases, the remote device can include a smartphone. In some cases, the first and second electronic subsystems can receive and process user information from the remote device.

In another aspects, a method of sensing at least two physiological parameters of a user can include positioning a first fitness tracker on a portion of the user's body with a first band, the first fitness tracker sensing a first physiological parameter of the user and wirelessly communicating signals responsive to the first physiological parameter to a remote device, the first fitness tracker including a first engagement surface; positioning a second fitness tracker on a portion of the user's body with a second band, the second fitness tracker sensing a second physiological parameter of the user and wirelessly communicating signals responsive to the second physiological parameter to the remote device, the second fitness tracker including a second engagement surface, the second engagement surface positioned adjacent to and interlocked with the first engagement surface to form the appearance of a unified enclosure for the first and second fitness trackers.

The method of any of the preceding paragraphs herein can include one or more of the following steps and/or features. In some cases, the first engagement surface can have at least a first selected contour and the second engagement surface can have at least a second selected contour. In some cases, the first selected contour and the second selected contour can be the same. In some cases, the first physiological parameter can be motion of the user. In some cases, the second physiological parameter can be a heartrate of the user. In some cases, the first physiological parameter can be a heartrate of the user. In some cases, the method can include positioning a third fitness tracker on a portion of the user's body with a third band, the third fitness tracker positioned between the first fitness tracker and the second fitness tracker, the third fitness tracker sensing a third physiological parameter of the user and wirelessly communicating signals responsive to the third physiological parameter to the remote device, the third fitness tracker including a third engagement surface and a fourth engagement surface, the third engagement surface positioned adjacent to and interlocked with the first engagement surface, the fourth engagement surface positioned adjacent to and interlocked with the second engagement surface, the first, second and third fitness trackers forming the appearance of a unified enclosure for the first and second fitness trackers.

In another aspects, a system can include a first wearable device including a first housing and a first strap configured to secure the first housing to a user's body, the first housing including a first sensor; and a second wearable device including a second housing and a second strap configured to secure the second housing to the user's body, the second housing including a second sensor that can be different than the first sensor; when the first and second wearable devices are secured to the user's body adjacent one another, a first portion of the first housing can contact a second portion of the second housing, said first and second portions can have complimentary shapes.

The system of any of the preceding paragraphs and/or any of the apparatuses, systems, or devices disclosed herein can include one or more of the following features. In some cases, the first sensor can sense a first physiological parameter of the user when the first wearable device is in use, and the second sensor can sense a second physiological parameter of the user when the second wearable device is in use. In some cases, the first physiological parameter can different than the second physiological parameter. In some cases, the first and second physiological parameters can include at least one of a blood oxygen saturation, a heart rate, a temperature, and a motion of the user. In some cases, each of the first portion of the first housing and the second portion of the second housing can be curved. In some cases, the first and second housings can be removably connect to each other. In some cases, the first strap can include a first plurality of magnets; the second strap can include a second plurality of magnets; each magnet of the first plurality of magnets and a corresponding magnet of the second plurality of magnets can have opposing poles; the first plurality of magnets and the second plurality of magnets can attach to each other and secure at least a portion of the first strap to at least a portion of the second strap. In some cases, the first and second straps can abut one another when the first and second portions of the first and second wearable housing contact one another. In some cases, the first and second housings can form a unified enclosure when the first and second housing are in contact with each other. In some cases, the first wearable device can include a first electronic subsystem configured to wirelessly communicate with a remote device; and the second wearable device can include a second electronic subsystem configured to wirelessly communicate with the remote device. In some cases, the system includes a third wearable device including a third housing and a third strap configured to secure the third housing to the user's body, the third housing including a third sensor that can be different than the first sensor; when the first, second, and third wearable devices are secured to the user's body adjacent one another, the first portion of the first housing can contact a third portion of the third housing and the second portion of the second housing can contact a fourth portion of the third housing, said first, second, third, and fourth portions can have complimentary shapes. In some cases, the first and third straps can abut one another when the first and third portions of the first and third wearable housings contact one another; and the second and third straps can abut one another when the second and fourth portions of the second and third wearable housings contact one another. In some cases, the first, second, and third housings can form a unified enclosure when the first, second, and third housing are in contact with each other.

In another aspects, the system can include a first wearable device including a first housing, the first housing comprising a first sensor; and a second wearable device including a second housing, the second housing comprising a second sensor that is different than the first sensor; the first and second wearable devices can be secured to a user's body adjacent one another, a first portion of the first housing can contact a second portion of the second housing, said first and second portions can have complimentary shapes; and the first and second housings can form a unified enclosure when the first and second housings are in contact with each other.

The system of any of the preceding paragraphs and/or any of the apparatuses, systems, or devices disclosed herein can include one or more of the following features. In some cases, each of the first portion of the first housing and the second portion of the second housing can be curved. In some cases, the system can include a third wearable device including a third housing, the third housing including a third sensor; when the first, second, and third wearable devices are secured to the user's body adjacent one another, the first portion of the first housing can contact a third portion of the third housing and the second portion of the second housing can contact a fourth portion of the third housing, said first, second, third, and fourth portions can have complimentary shapes; and the first, second, and third housings can form a unified enclosure when the first, second, and third housings are in contact with each other.

In another aspects, a system can include a first wearable device including a first housing and a first strap to secure the first housing to a user's body, the first housing including a first sensor; a second wearable device including a second housing and a second strap to secure the second housing to the user's body, the second housing including a second sensor that can be different than the first sensor; when the first and second wearable devices are secured to the user's body adjacent one another, portions of the first and second housings can contact one another along an abutment juncture having a serpentine shape.

In another aspects, a wearable device including at least a first operational mode and a second operational mode can include a first screen display to display images representing data and graphic information in the first operational mode; and a second screen display overlaying the first screen display to display low refresh rate images in the second operational mode, the second screen display can be transparent in the first operational mode such that images displayed by the first display are visible through the second display in the first operational mode.

The wearable device of any of the preceding paragraphs and/or any of the apparatuses, systems, or devices disclosed herein can include one or more of the following features. In some cases, the wearable device can include a switch to transition the wearable device from the first operational mode to the second operational mode and vice versa. In some cases, the wearable device can include at least one sensor to detect a physiological parameter of a user when the wearable device is in use. In some cases, the physiological parameter can include at least one of a blood oxygen saturation, a heart rate, a temperature, and a motion of the user. In some cases, the first screen display can include an OLED display. In some cases, the second screen display can include a reflective display including a plurality of ink particles. In some cases, the wearable device can include an electric circuitry to selectively charge the ink particles of the reflective display in the second operational mode. In some cases, a shape of the first screen display and a shape of the second screen display are the same. In some cases, the wearable device consumes more power when the wearable device is in the first operational mode than when the wearable device is in the second operational mode. In some cases, the wearable device can include a band for securing the wearable device to a portion of a user's body, the band including a first end and a second end, wherein the first end can attach to a first end of the wearable device and the second end can attach to a second end of the wearable device.

In another aspects, a method of operating a smartwatch in two operational modes can include activating an e-ink display screen in a first operational mode, the smartwatch sending commands to the e-ink display screen in the first operational mode to cause the e-ink display screen to display images representing an analog watch; and switching the smartwatch to a second operational mode, the smartwatch deactivating the e-ink display screen in the second operational mode to cause the e-ink display to become transparent, the smartwatch activating an interactive display screen to display information on the interactive screen and to receive tactile inputs via the interactive display screen, the information visible through the transparent e-ink display screen in the second operational mode.

One aspect of the embodiments disclosed herein is a smartwatch that includes a housing having a lower base portion and an upper removable portion. The base portion is secured to a band configured to engage a portion of a user's limb. A lower surface of the base portion includes at least one sensor configured to contact the user's skin and to sense a physiological parameter. A first electronic subsystem within the base portion processes sensed signals from the at least one sensor and selectively generates a wireless communication signal in response to the sensed signals. The first electronic subsystem is powered by a first battery within the base portion. A second electronic subsystem within the removable portion is powered by a second battery, which is selectively couplable to an external charger when the removable portion is removed from the base portion. The second battery charges the first battery when the removable portion is attached to the base portion.

Another aspect in accordance with embodiments disclosed herein is a smartwatch that includes a base housing portion secured to a band. The band is configured to engage a portion of a user's limb. The base housing portion has a lower surface. The lower surface has at least one sensor configured to contact the user's skin and to sense a physiological parameter. A first electronic subsystem within the base housing portion is configured to process sensed signals from the at least one sensor and to selectively generate a wireless communication signal in response to the sensed signals. A first battery within the base portion is configured to provide power to the first electronic subsystem. A removable housing portion is attachable to the base housing portion. The removable housing portion has a visual display. The removable housing portion includes a second electronic subsystem. The second electronic system is powered by a second battery. The second battery is selectively couplable to an external charger when the removable housing portion is removed from the base portion. The second battery within the removable housing portion charges the first battery within the base housing portion when the removable housing portion is attached to the base housing portion. In certain embodiments, the base housing portion wirelessly communicates with removable housing portion.

Another aspect of the embodiments disclosed herein is a method of charging a smartwatch. The method includes detaching a removable housing portion of the smartwatch from a base housing portion of the smartwatch. The removable housing portion encloses a main battery therein. The base housing portion encloses an auxiliary battery therein. The method further includes positioning the removable housing portion of the smartwatch on a charging source to charge the main battery. The method further includes maintaining the base housing portion in sensory communication with a user while the removable housing portion is detached. The base housing portion receives power from the auxiliary battery when the removable housing portion is detached from the base housing portion. The method further includes reattaching the removable housing portion to the base housing portion after charging the main battery. The method further includes charging the auxiliary battery with energy from the main battery when the removable housing portion is attached to the base housing portion. In certain embodiments, the base housing portion wirelessly communicates with the removable housing portion while the removable housing portion is removed from the base housing portion.

Another aspect of the embodiments disclosed herein is a smartwatch including a smartwatch body and a removable battery pack. The smartwatch body houses an internal battery. The smartwatch body includes at least first input electrode positioned on a first portion of the smartwatch body and a second input electrode positioned on a second portion of the smartwatch body. The removable battery pack is selectively attachable to the smartwatch body. The removable battery pack has a plurality of engagement surfaces that engage the smartwatch body to removably secure the removable battery pack to the smartwatch body. The removable battery pack includes at least first output electrode and a second output electrode. The first output electrode is positioned on the removable battery pack such that the first output electrode contacts the first input electrode of the smartwatch when the removable battery pack is secured to the smartwatch body and such that the second output electrode contacts the second input electrode of the smartwatch body when the removable battery pack is secured to the smartwatch body. The removable battery pack provides electrical power via the contacts between the output electrodes and the input electrodes to charge the internal battery within the smartwatch body. In certain embodiments, the first output electrode is positioned on a first engagement surface of the plurality of engagement surfaces, and the second output electrode is positioned on a second engagement surface of the plurality of engagement surfaces. In certain embodiments, the smartwatch body further includes a third input electrode and a fourth input electrode. The removable battery pack further includes a third output electrode positioned on a third engagement surface of the plurality of engagement surfaces and includes a fourth output electrode positioned on a fourth engagement surface of the plurality of engagement surfaces. The third output electrode contacts the third input electrode and the fourth output electrode contacts the fourth input electrode when the removable battery pack is secured to the smartwatch body.

Another aspect of the embodiments disclosed herein is a method of charging a smartwatch while the smartwatch is being worn by a user. The method includes attaching a charged removable battery pack to a body of the smartwatch by positioning a plurality of engagement surfaces against respective portions of the body of the smartwatch. The method further includes engaging a first output electrode of the removable battery pack with a first input electrode of the body of the smartwatch to provide a first electrical contact between the first output electrode and the first input electrode. The method further includes engaging a second output electrode of the removable battery pack with a second input electrode of the body of the smartwatch to provide a second electrical contact between the second output electrode and the second input electrode. The method further includes charging a battery within the smartwatch body with power from a battery within the removable battery pack by propagating electrical energy via the first electrical contact and the second electrical contact. In certain embodiments, the first output electrode is positioned on a first engagement surface of the plurality of engagement surfaces, and the second output electrode is positioned on a second engagement surface of the plurality of engagement surfaces. In certain embodiments, the method further includes engaging a third output electrode of the removable battery pack with a third input electrode of the body of the smartwatch to provide a third electrical contact between the third output electrode and the third input electrode; and engaging a fourth output electrode of the removable battery pack with a fourth input electrode of the body of the smartwatch to provide a fourth electrical contact between the fourth output electrode and the fourth input electrode. In certain embodiments, the first output electrode is positioned on a first engagement surface of the plurality of engagement surfaces; the second output electrode is positioned on a second engagement surface of the plurality of engagement surfaces; the third output electrode is positioned on a third engagement surface of the plurality of engagement surfaces; and the fourth output electrode is positioned on a fourth engagement surface of the plurality of engagement surfaces.

One aspect of the embodiments disclosed herein is a fitness tracker having an enclosure secured to a band configured to engage a portion of a user's limb. The enclosure houses at least one sensor to sense a physiological parameter of the user. The enclosure is configured to have a shape selected to provide an aesthetic appearance that may have the appearance of a gem or other item of jewelry. The enclosure has at least one peripheral surface having preselected contours. The contours are selected such that the contours of the peripheral surface of a first enclosure of a first fitness tracker are engageable with the contours of the peripheral surface of a second enclosure of an adjacent fitness tracker such that the two enclosures appear as a single enclosure. Each enclosure includes a respective electronic system that communicates wirelessly with a remote device such as a smartphone.

Another aspect in accordance with embodiments disclosed herein is a system of at least a first fitness tracker and a second fitness tracker. Each fitness tracker is capable of wirelessly communicating a respective physiological parameter of a user to a remote device. The systems includes a first enclosure of the first fitness tracker. The first enclosure is couplable to a first band configured to attach to a limb of a user. A first electronic subsystem within the first enclosure is configured to sense a first physiological parameter of the user when attached to the user. The first electronic subsystem is configured to wirelessly transmit signals responsive to the first physiological parameter. An upper portion of the first enclosure has at least a first engagement surface. The first engagement surface has at least one selected contour. A second enclosure of the second fitness tracker is couplable to a second band configured to attach to the limb of the user. A second electronic subsystem within the second enclosure is configured to sense a second physiological parameter of the user when attached to the user. The second electronic subsystem is configured to wirelessly transmit signals responsive to the second physiological parameter. An upper portion of the second enclosure has at least a second engagement surface. The second engagement surface has at least a second selected contour. The second selected contour is selected with respect to the first selected contour such that the second engagement surface of the second enclosure interlocks with the first engagement surface of the first enclosure. In certain embodiments of the system, the at least one first selected contour and the at least one second selected contour are the same. In certain embodiments of the system, the first physiological parameter is motion of the user, and the second physiological parameter is a heartrate of the user. In certain embodiments of the system, the first physiological parameter is a heartrate of the user.

In certain embodiments, the system further includes a third fitness tracker positionable between the first fitness tracker and the second fitness tracker. The third fitness tracker includes a third enclosure couplable to a third band configured to attach to the limb of the user. A third electronic subsystem within the third enclosure is configured to sense a third physiological parameter of the user when attached to the user. The third electronic subsystem is configured to wirelessly transmit signals responsive to the third physiological parameter. An upper portion of the third enclosure has at least a third engagement surface and a fourth engagement surface. The third engagement surface has at least a third selected contour. The third selected contour is selected with respect to the first selected contour such that the third engagement surface of the third enclosure interlocks with the first engagement surface of the first enclosure. The fourth engagement surface has at least a fourth selected contour. The fourth selected contour is selected with respect to the second selected contour such that the fourth engagement surface of the third enclosure interlocks with the second engagement surface of the second enclosure.

Another aspect in accordance with embodiments disclosed herein is a method of sensing at least two physiological parameters of a user. The method includes positioning a first fitness tracker on a limb of a user with a first band. The first fitness tracker senses a first physiological parameter of the user and wirelessly communicates signals responsive to the first physiological parameter to a remote device. The first fitness tracker has a first upper enclosure having a first engagement surface. The method further includes positioning a second fitness tracker on the limb of a user with a second band. The second fitness tracker senses a second physiological parameter of the user and wirelessly communicates signals responsive to the second physiological parameter to the remote device. The second fitness tracker has a second upper enclosure having a second engagement surface. The second engagement surface of the second enclosure is positioned adjacent to and interlocks with the first engagement surface of the first enclosure to form the appearance of a unified upper enclosure for the first and second fitness trackers. In certain embodiments of the method, the first engagement surface has at least a first selected contour and the second engagement surface has at least a second selected contour. In certain embodiments of the method, the first selected contour and the second selected contour are the same. In certain embodiments of the method, the first physiological parameter is motion of the user, and the second physiological parameter is a heartrate of the user. In certain embodiments of the method, the first physiological parameter is a heartrate of the user.

In certain embodiments, the method further includes positioning a third fitness tracker on the limb of a user with a third band. The third fitness tracker is positioned between the first fitness tracker and the second fitness tracker. The third fitness tracker senses a third physiological parameter of the user and wirelessly communicates signals responsive to the third physiological parameter to the remote device. The third fitness tracker has a third upper enclosure having a third engagement surface and a fourth engagement surface. The third engagement surface of the third enclosure is positioned adjacent to and is interlocked with the first engagement surface of the first enclosure. The fourth engagement surface of the third enclosure is positioned adjacent to and is interlocked with the second engagement surface of the second enclosure. The first, second and third enclosures form the appearance of a unified upper enclosure for the first, second and fitness trackers.

One aspect of the embodiments disclosed herein is a smartwatch having a first interactive screen display that displays fitness information and other information generated by an internal processor in response to user commands. The smartwatch has a second display overlaying the interactive display, the second display displaying low refresh rate and/or low resolution metrics, such as time of day using symbols representing a time display of a conventional wristwatch. The second display can be based on low power consumption technologies, such as e-paper technology. The second display hides the first interactive screen display in a time display mode. A user may switch the smartwatch to a smartwatch mode to activate the interactive screen display and to cause the second display to become effectively transparent to enable the user to view the interactive screen display and to enter commands via the interactive screen display.

Another aspect in accordance with embodiments disclosed herein is a smartwatch having at least a first operational mode and a second operational mode. The smart watch includes a first screen display that displays images representing data and graphic information in the first operational mode. The smartwatch further includes a second screen display overlaying the first screen display. The second screen display includes e-ink technology. The second screen display is configured to display images representing an analog watch in the second operational mode. The second screen display is configured to be transparent in the first operational mode such that images displayed by the first screen display are visible through the second screen display when the smartwatch is in the first operational mode.

Another aspect in accordance with embodiments disclosed herein is a method of operating a smartwatch in two operational modes. The method includes activating an e-ink display screen in a first operational mode. The smartwatch sends commands to the e-ink display screen in the first operational mode to cause the e-ink display screen to display images representing the hands of an analog watch. The method further includes switching the smartwatch to a second operational mode. The smartwatch deactivates the e-ink display screen in the second operational mode to cause the e-ink display to become transparent. The smartwatch activates an interactive display screen to display information on the interactive screen and to receive tactile inputs via the interactive display screen. The information displayed by the interactive screen display is visible through the transparent e-ink display screen in the second operational mode.

BRIEF DESCRIPTIONS OF THE DRAWINGS

The foregoing aspects and other aspects of the disclosure are described in detail below in connection with the accompanying drawings in which:

FIG. 1 further illustrating a smartphone in wireless communication with the smartwatch;

Figure 7:
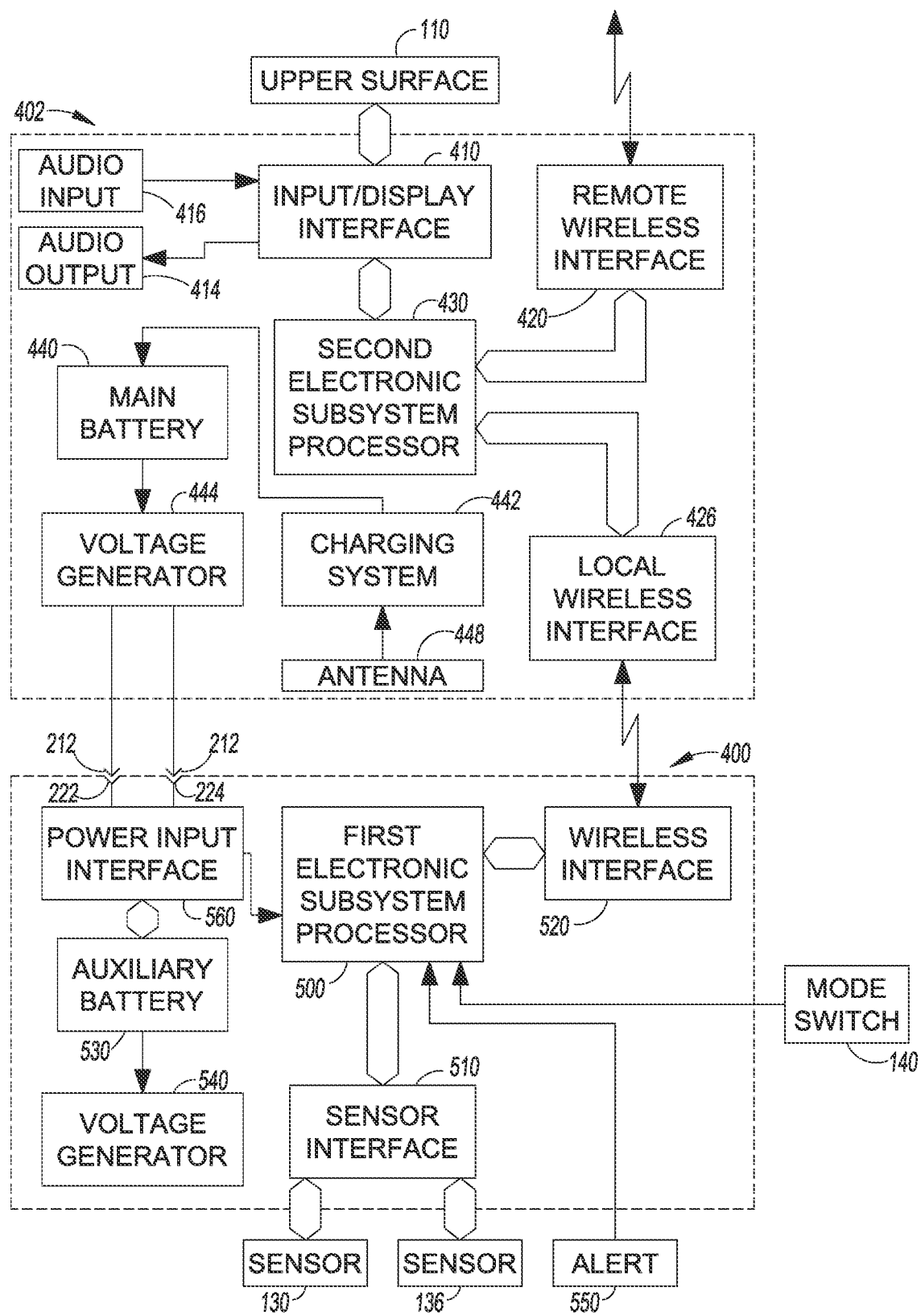
Figure 8:
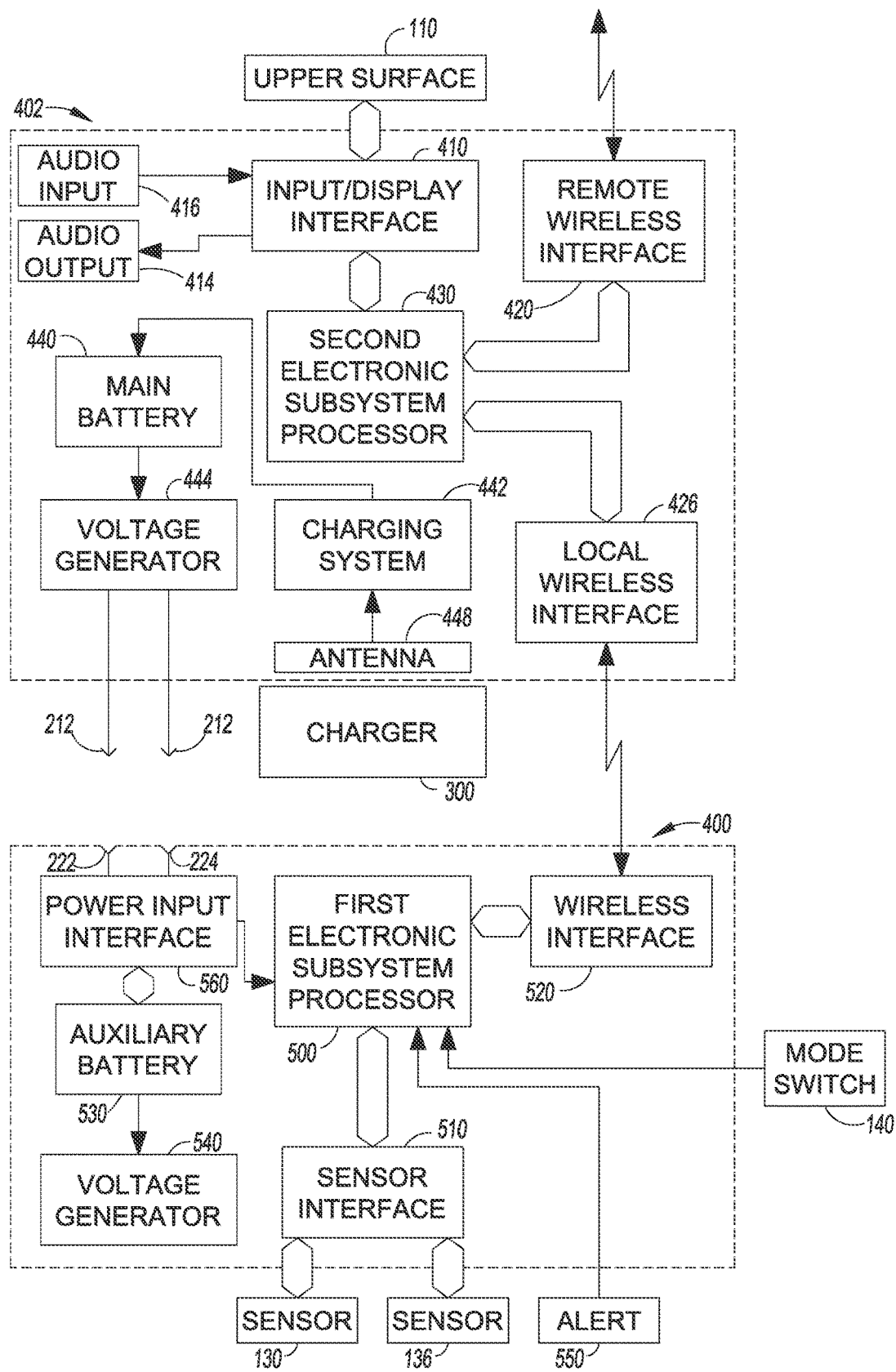
Figure 9:
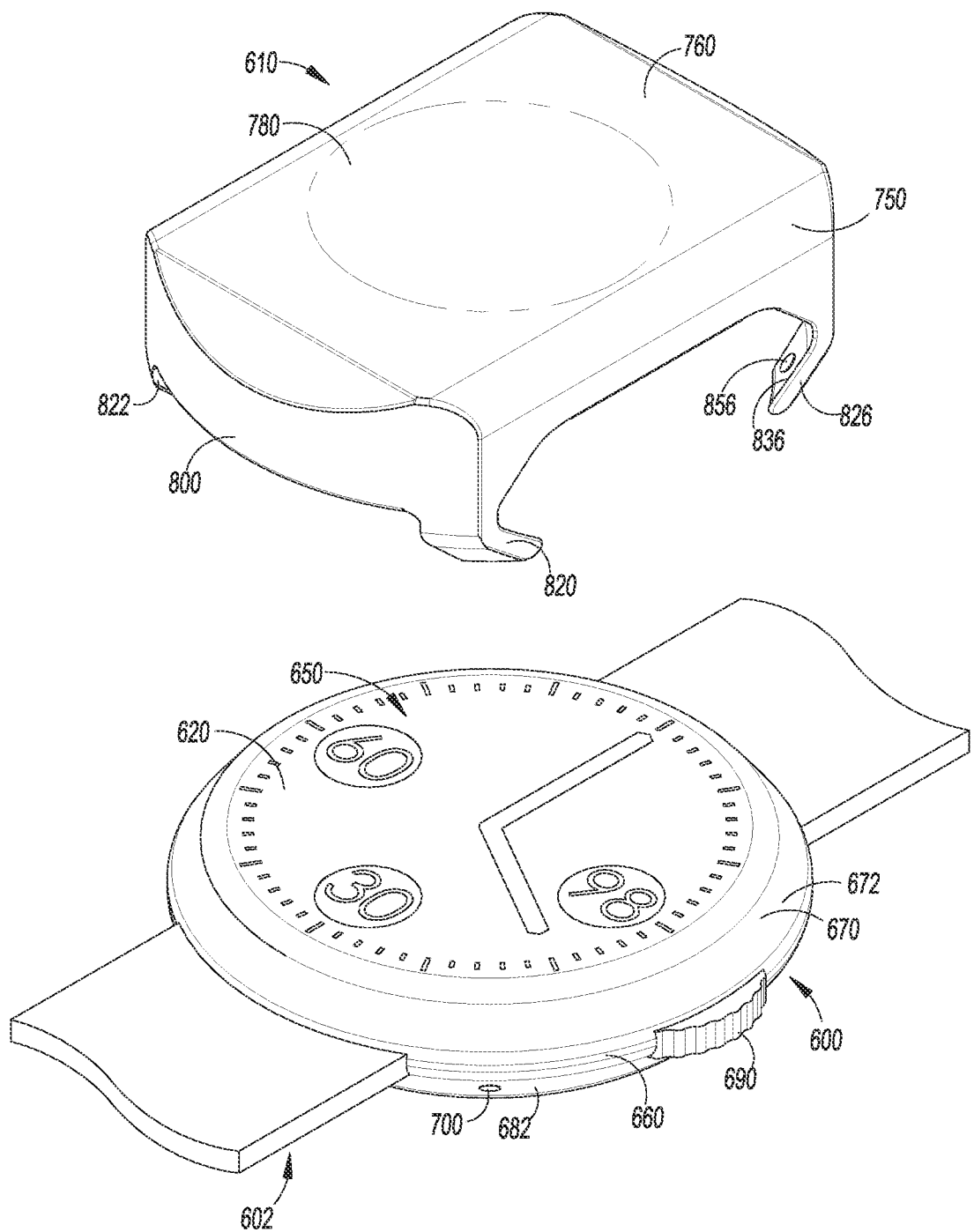
Figure 10:
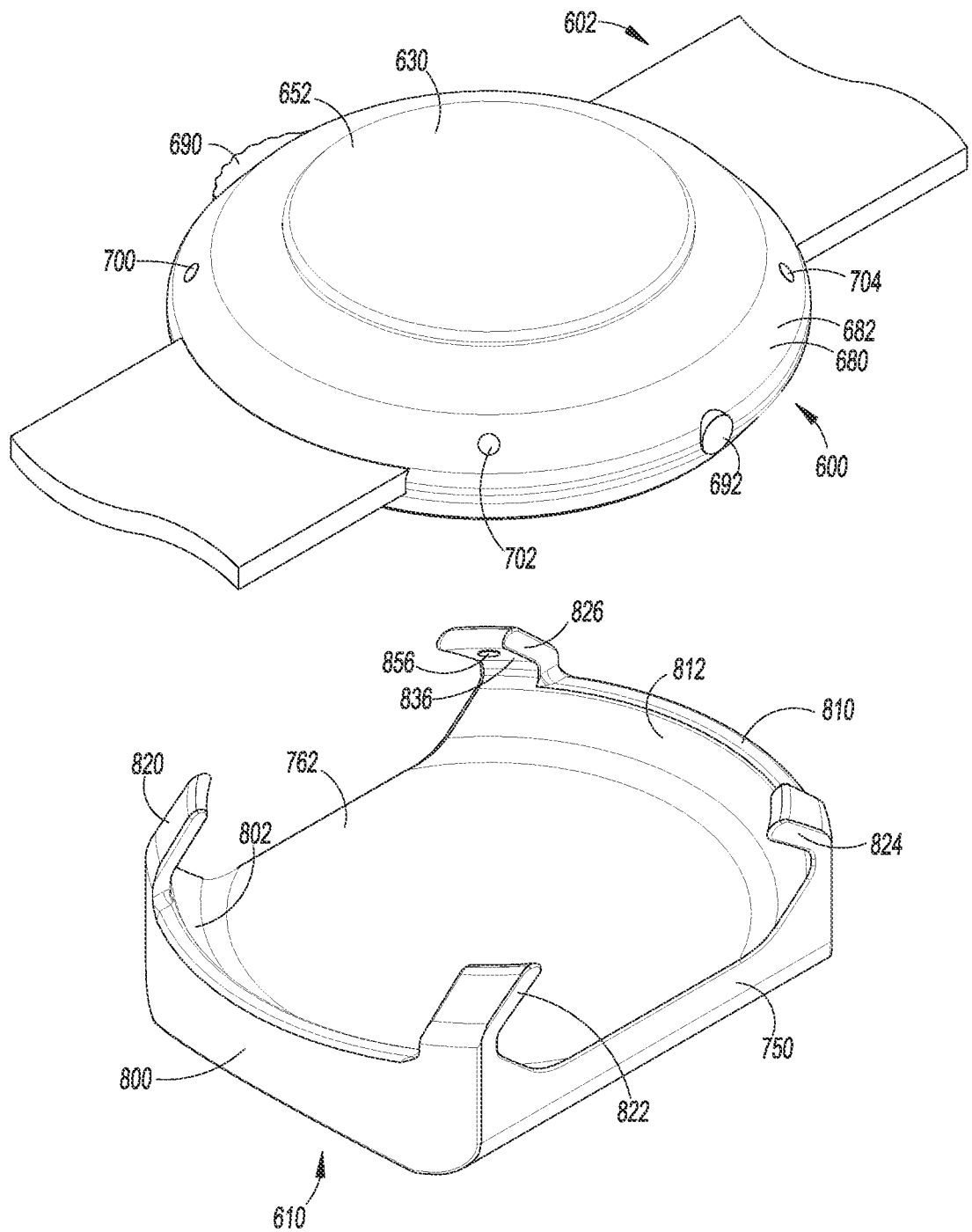
Figure 11:
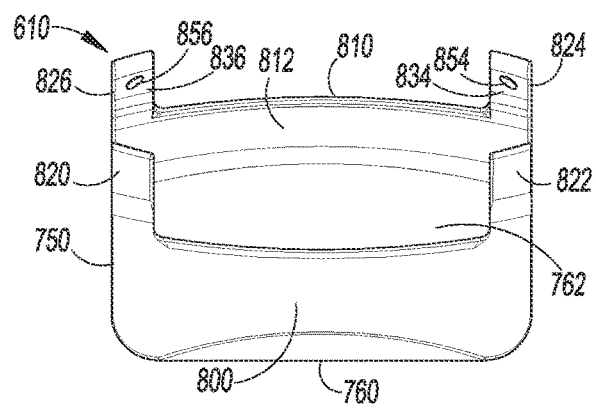
Figure 12:
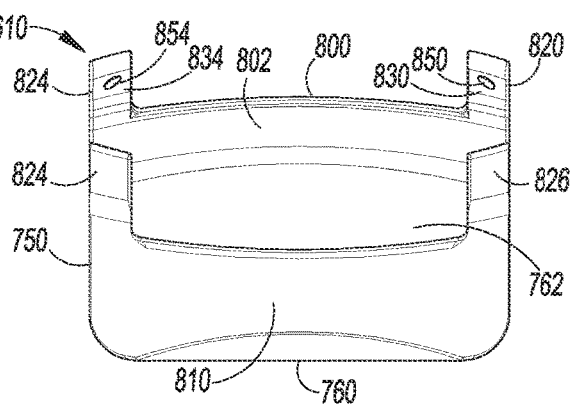
Figure 13:
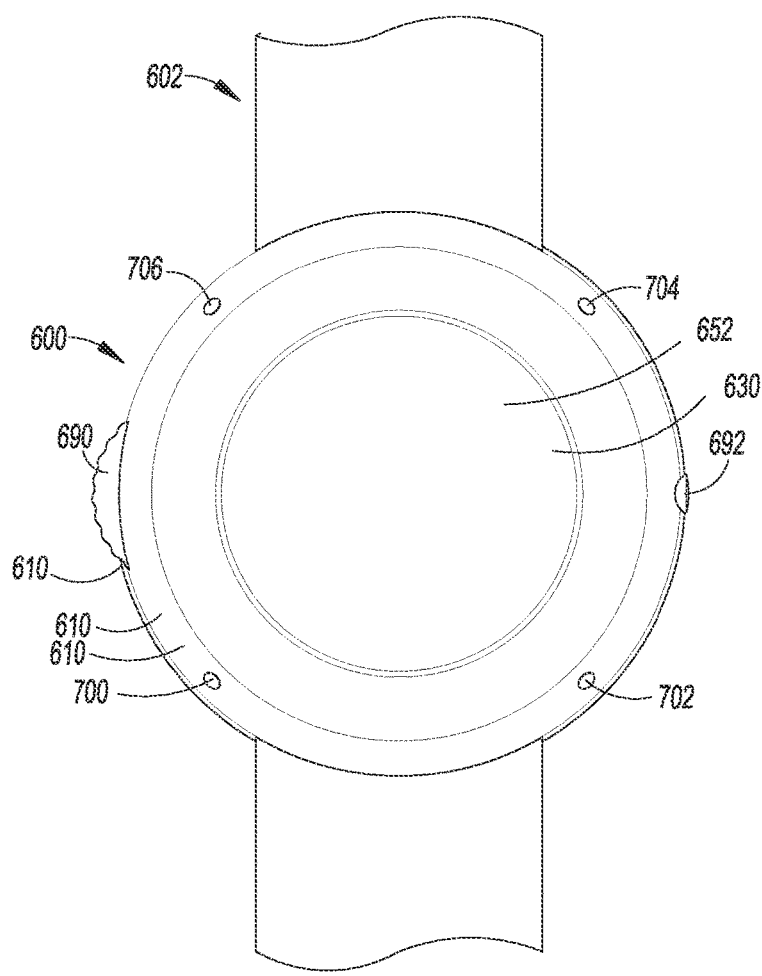
Figure 14:
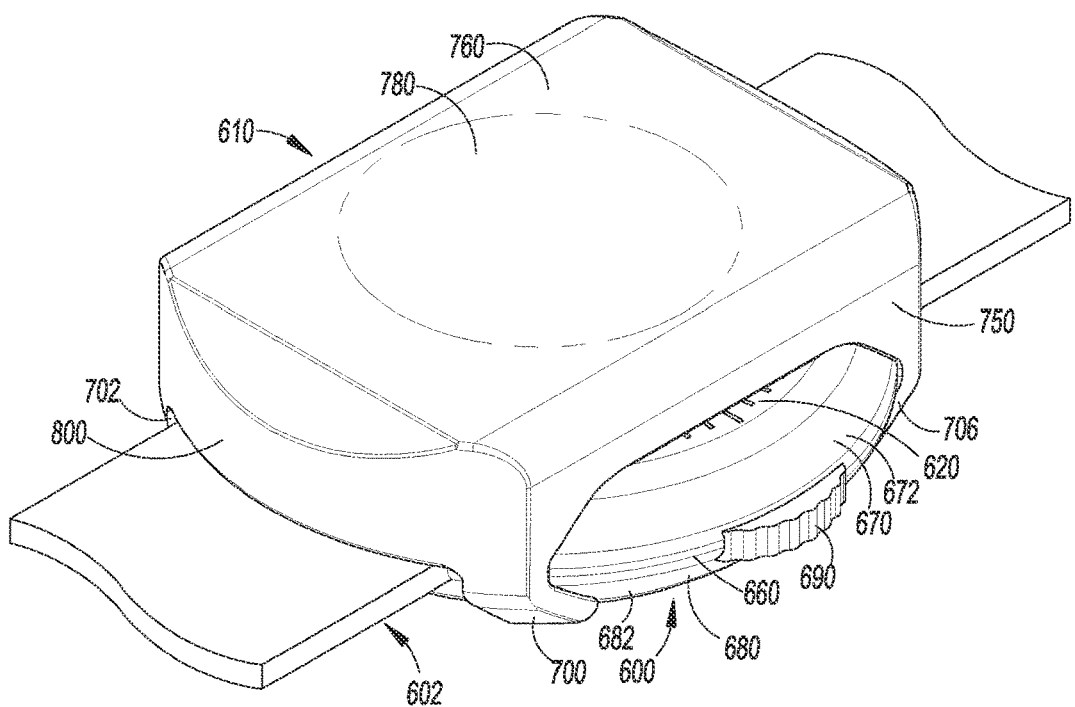
Figure 15:
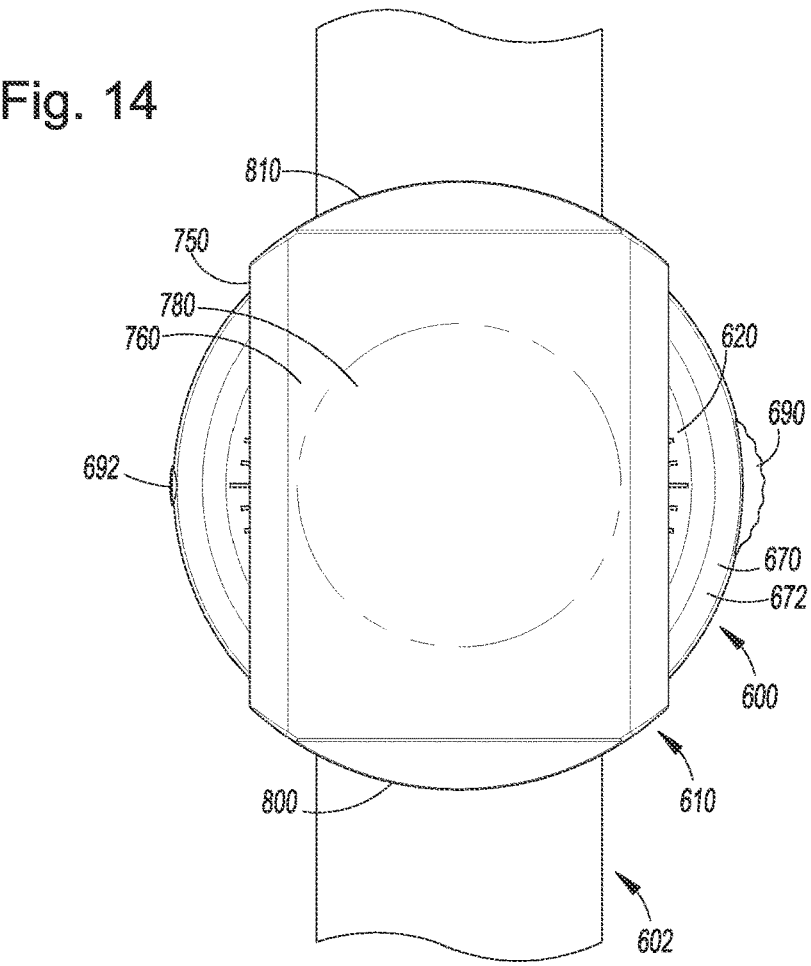
Figure 16:
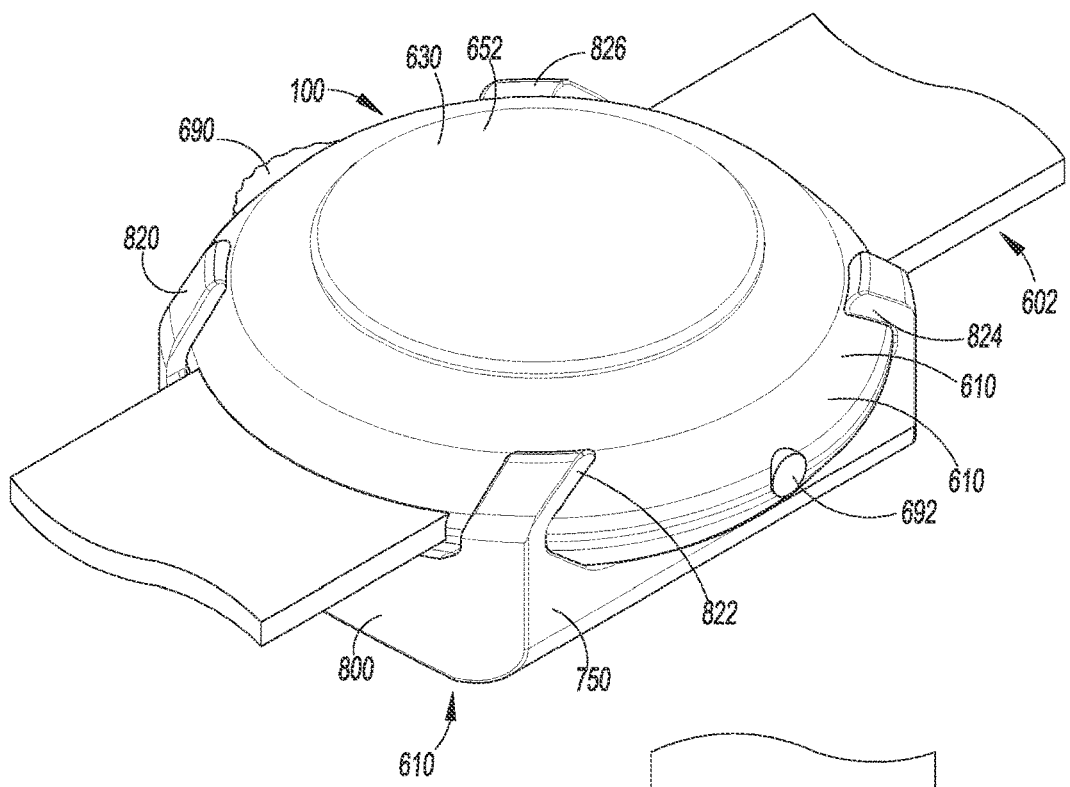
Figure 17:
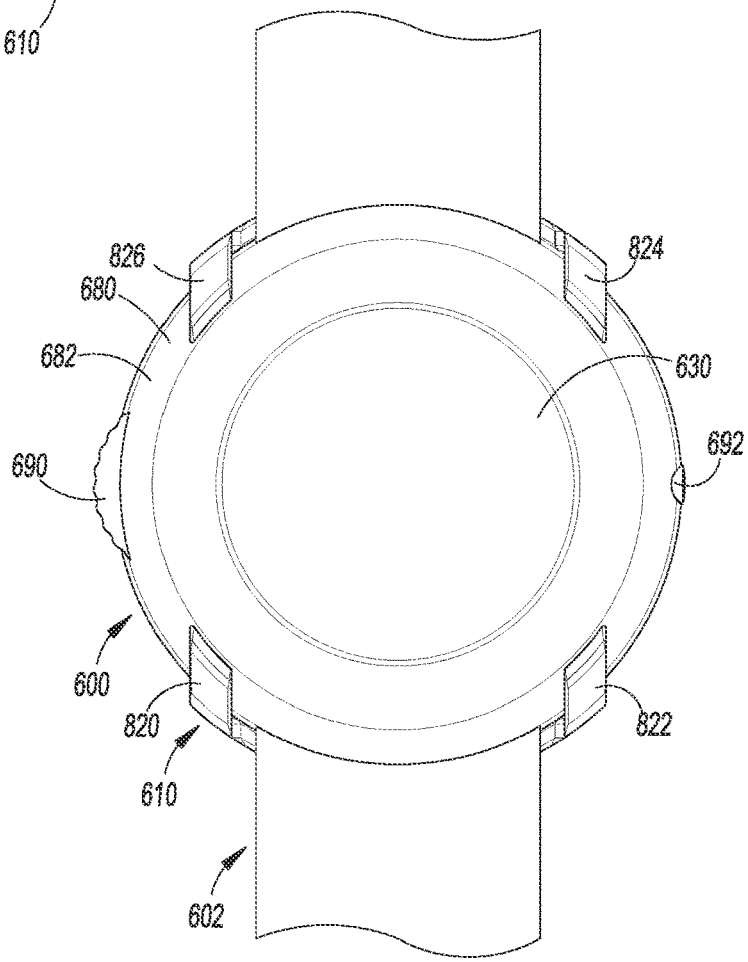
Figure 18:
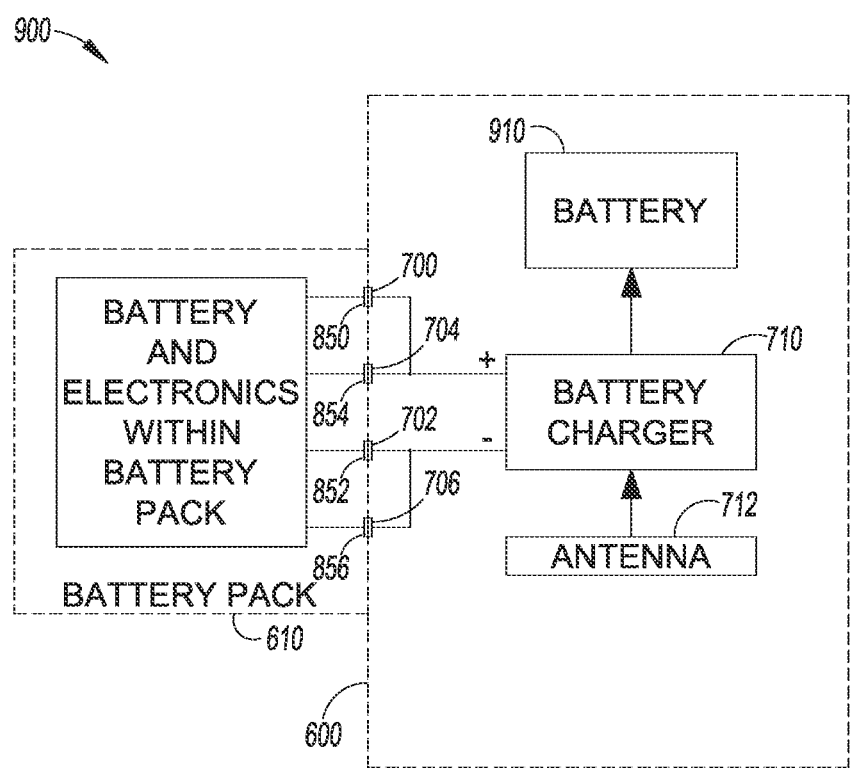
Figure 19:
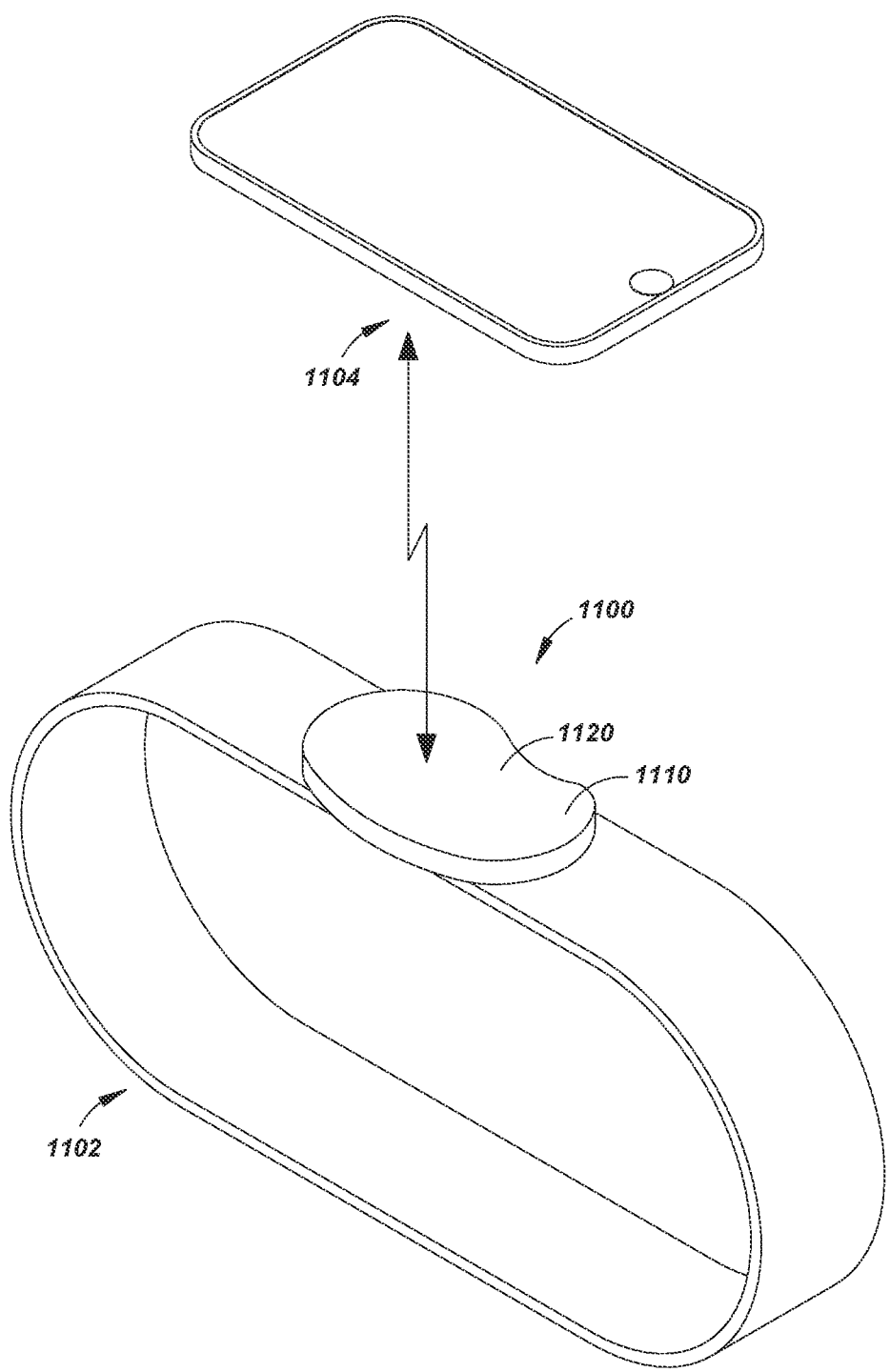
Figure 20:
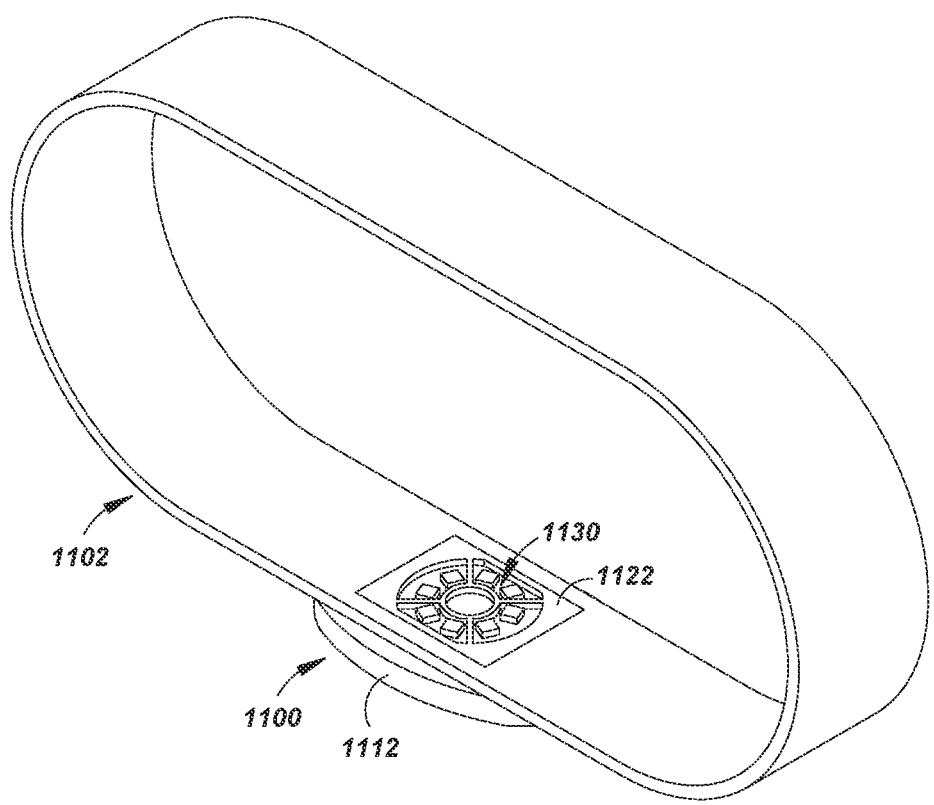
Figure 21:
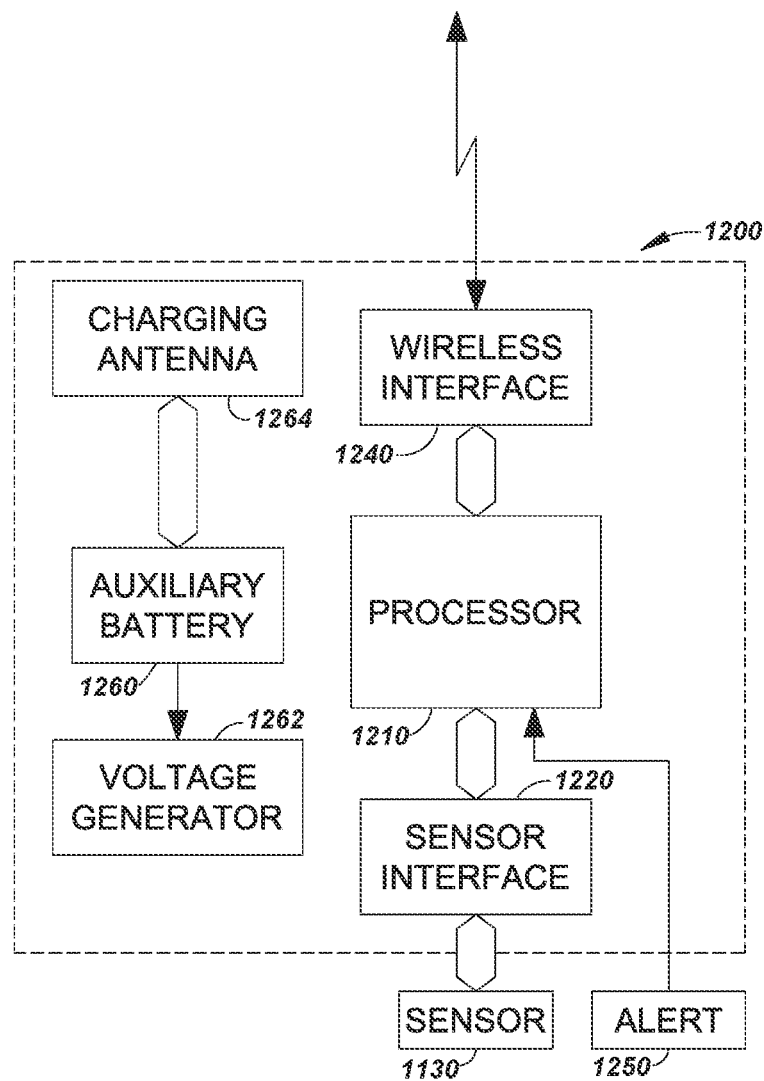
Figure 22:
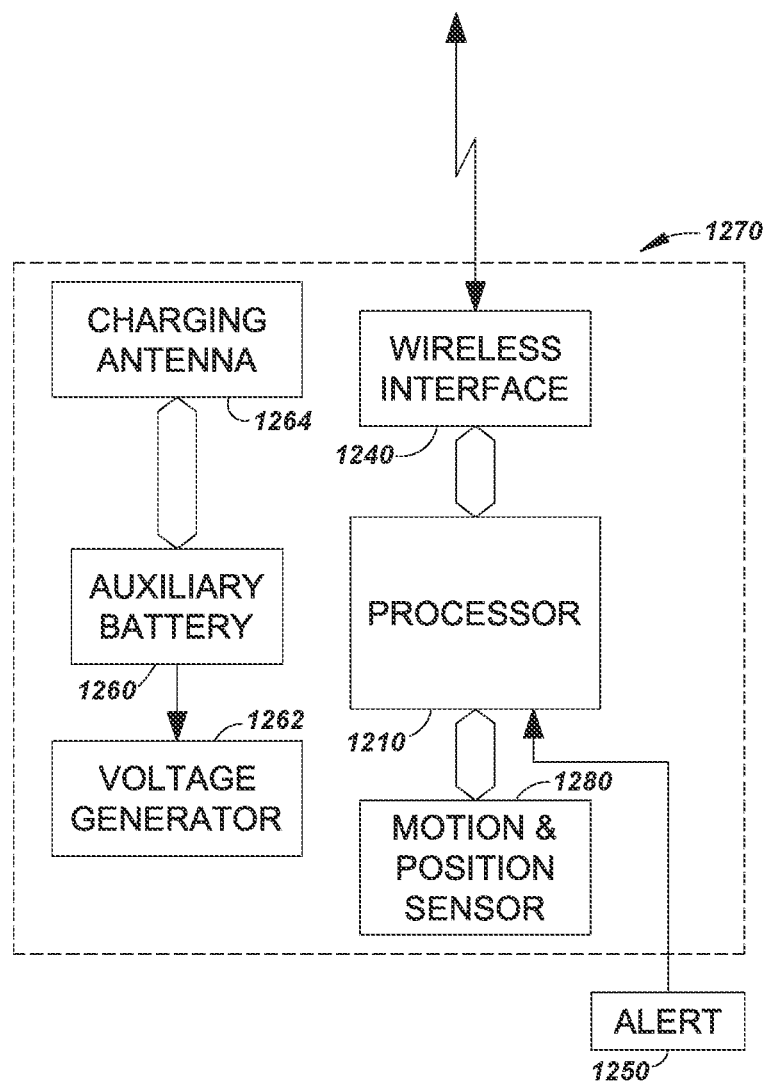
Figure 23:
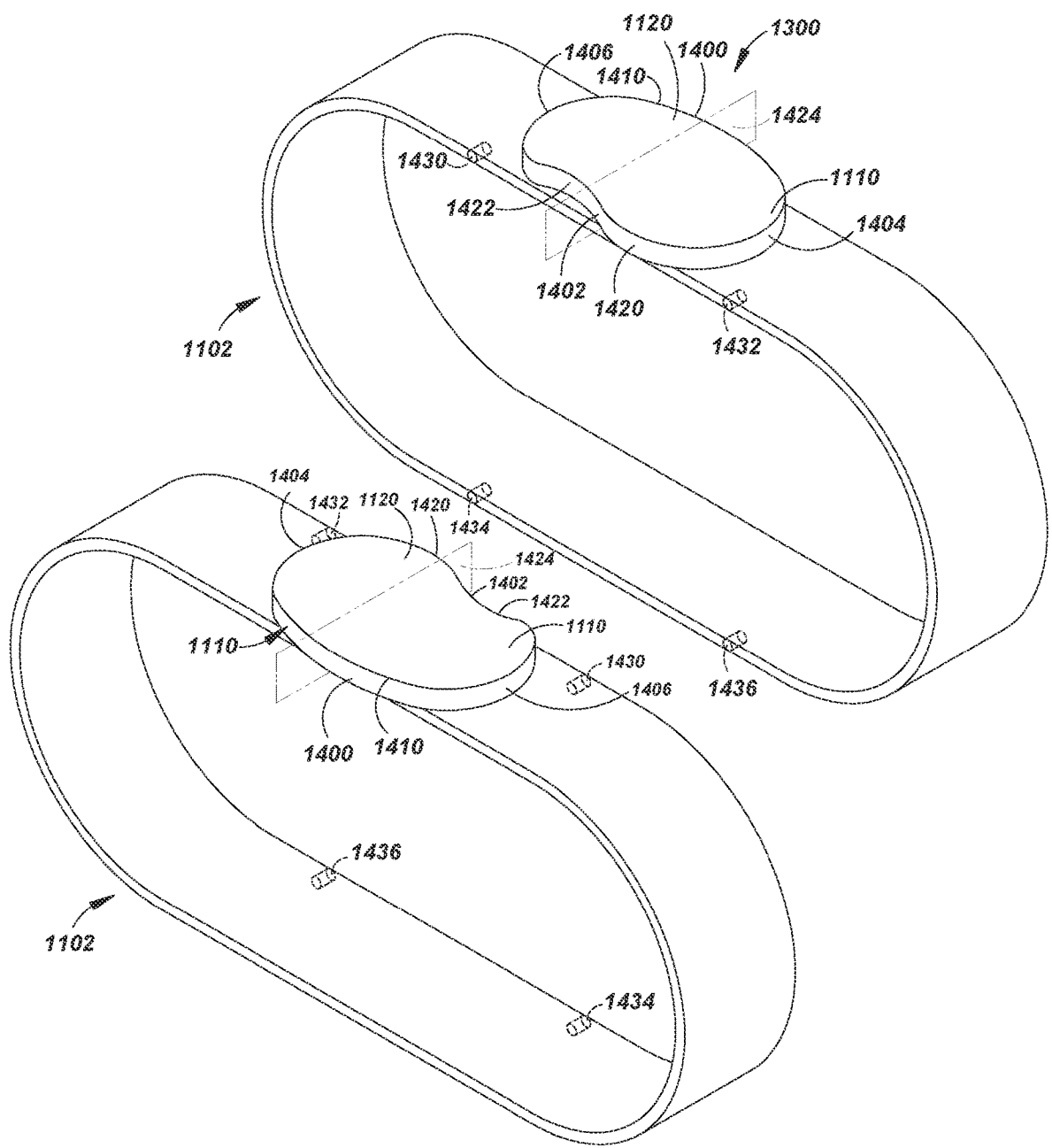
Figure 24:
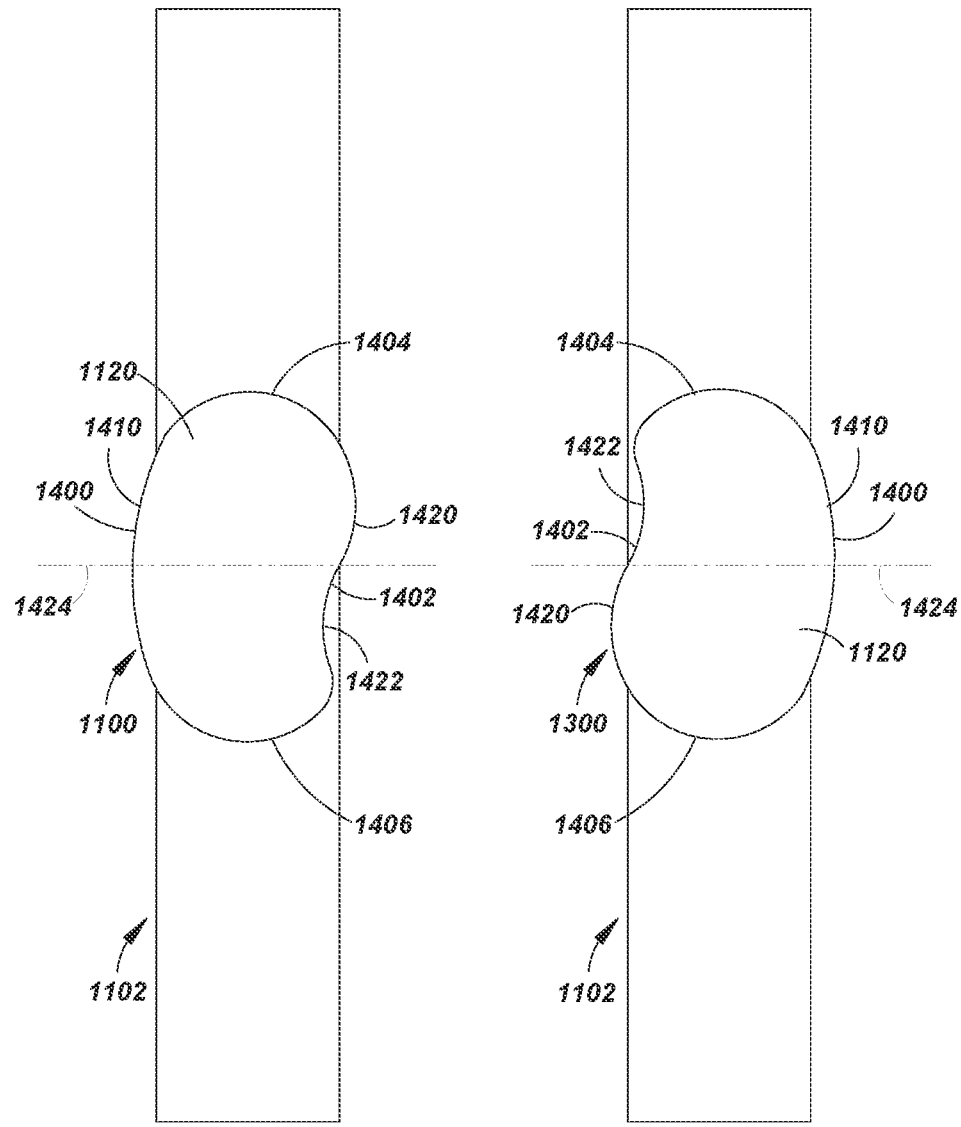
Figure 25:
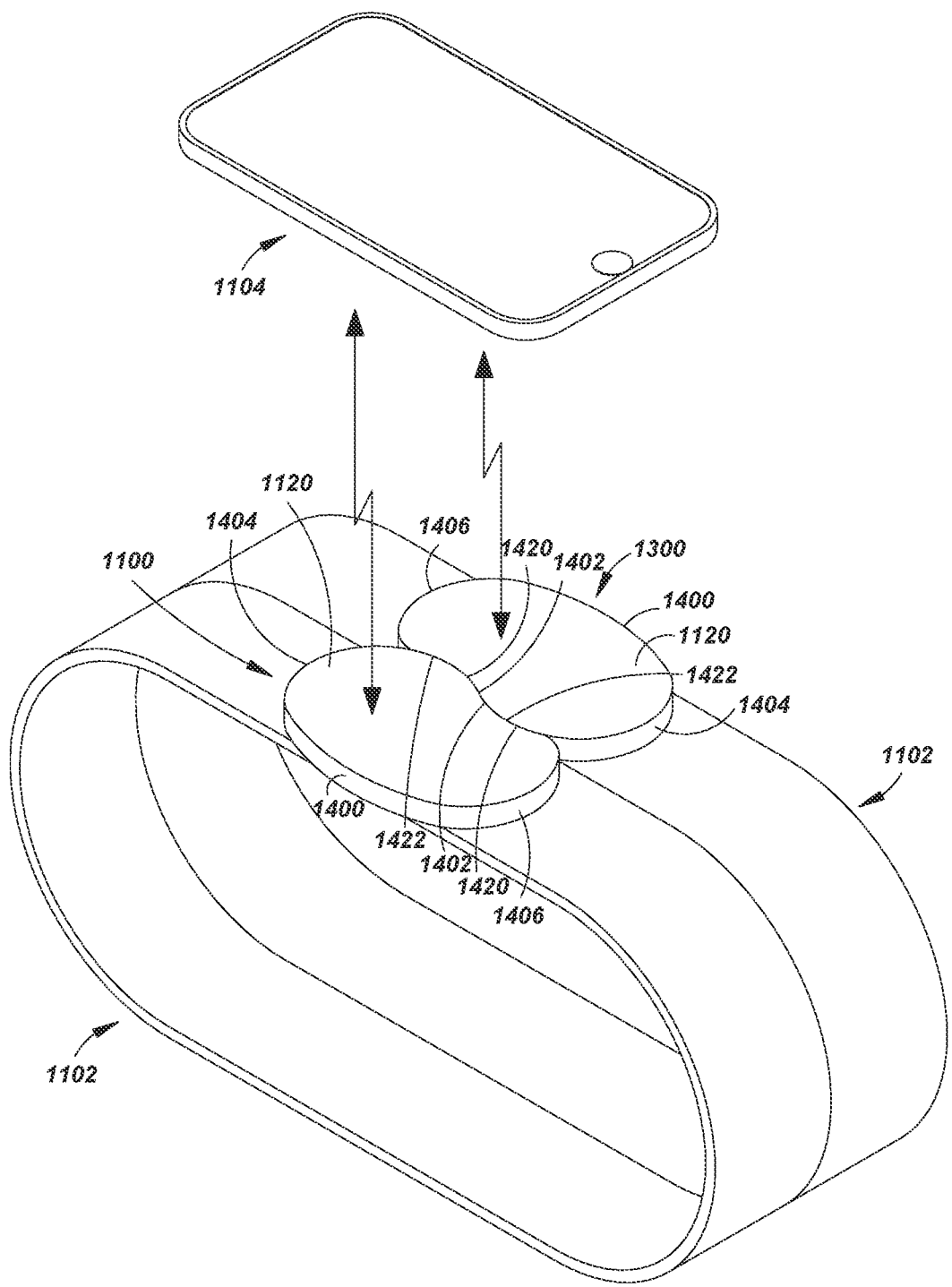
Figure 26:
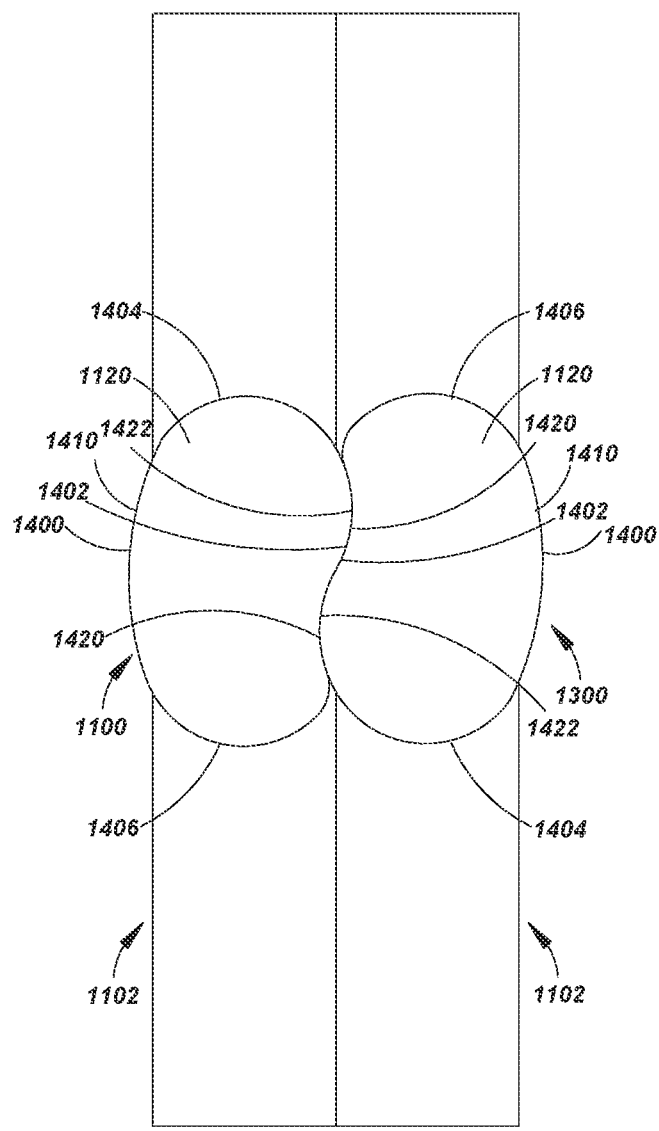
Figure 27:
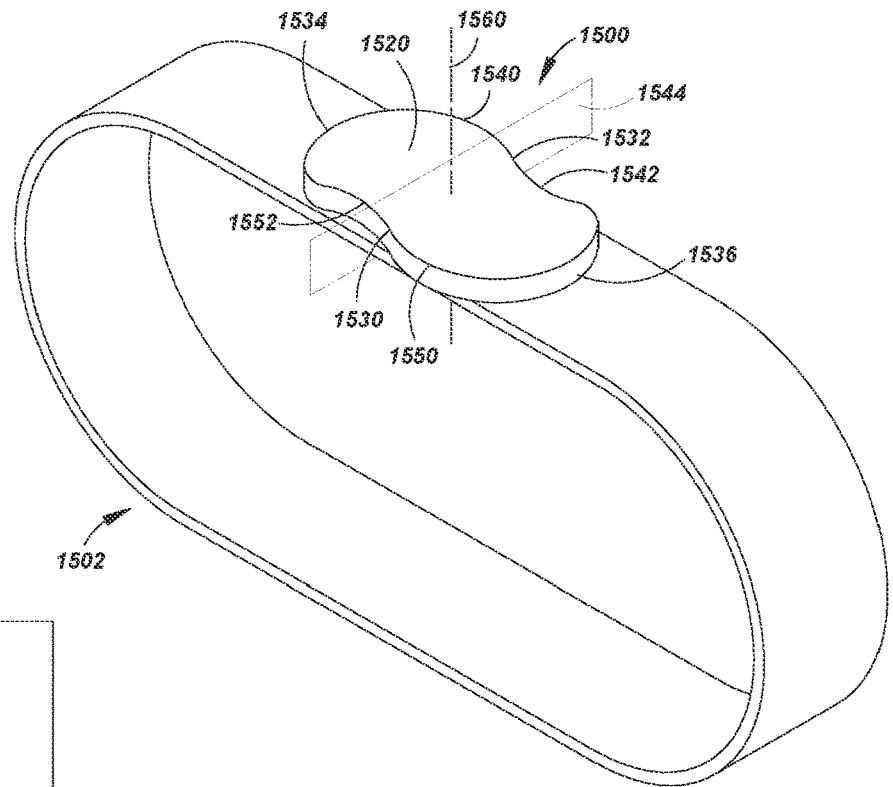
Figure 28:
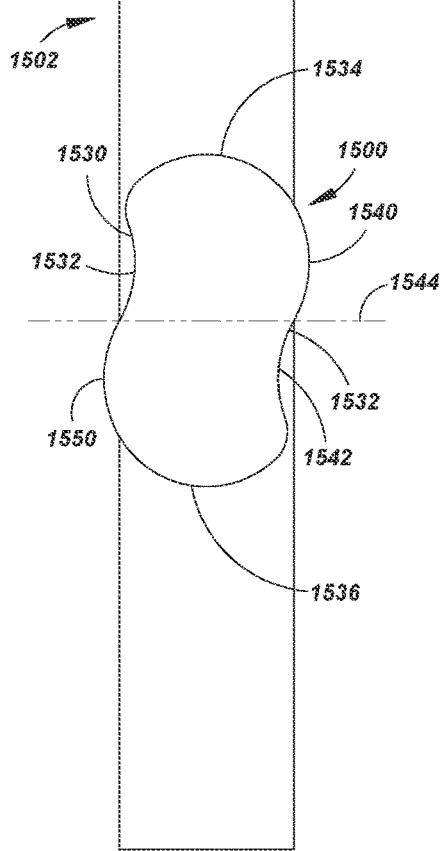
Figure 29:
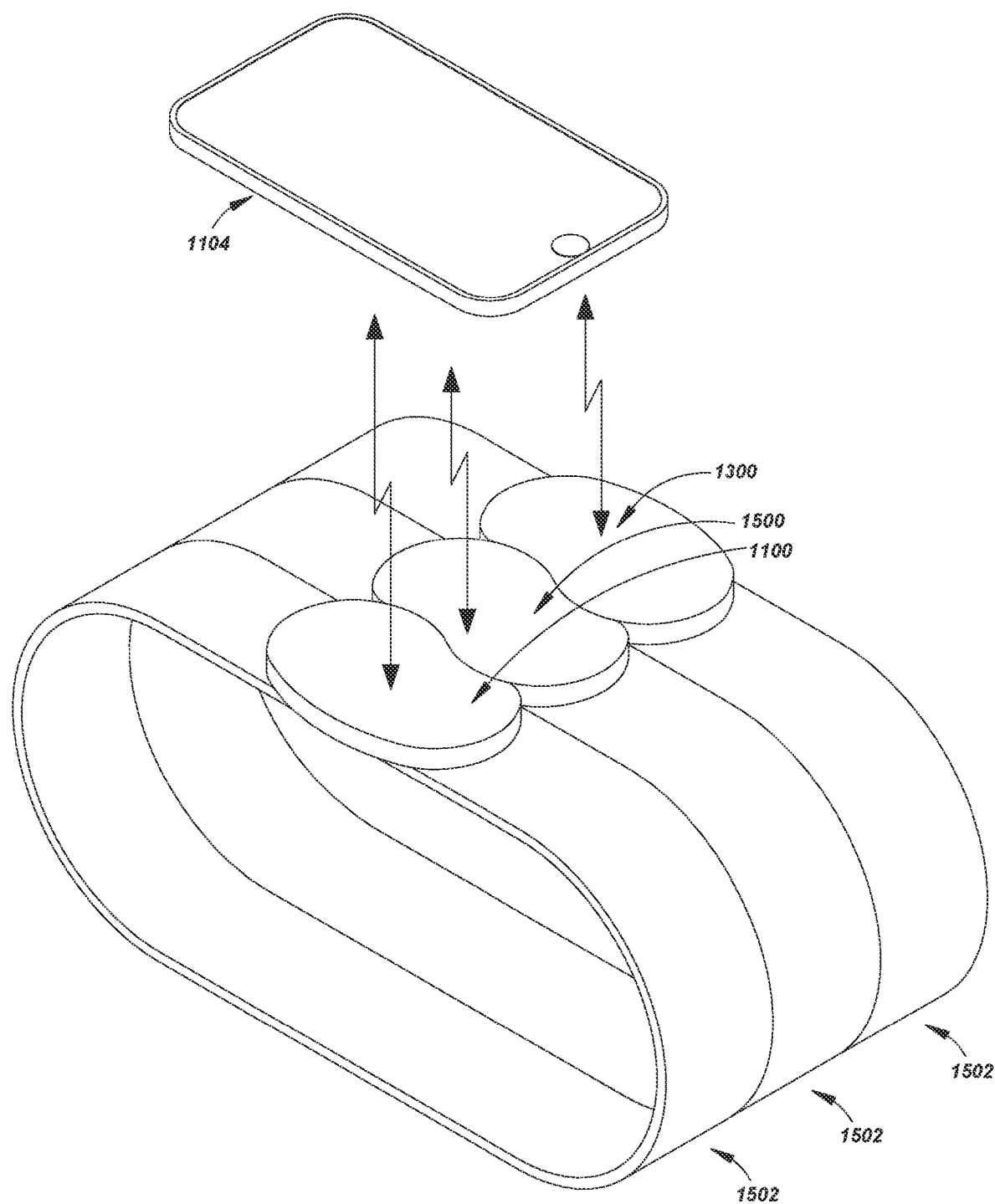
Figure 30:
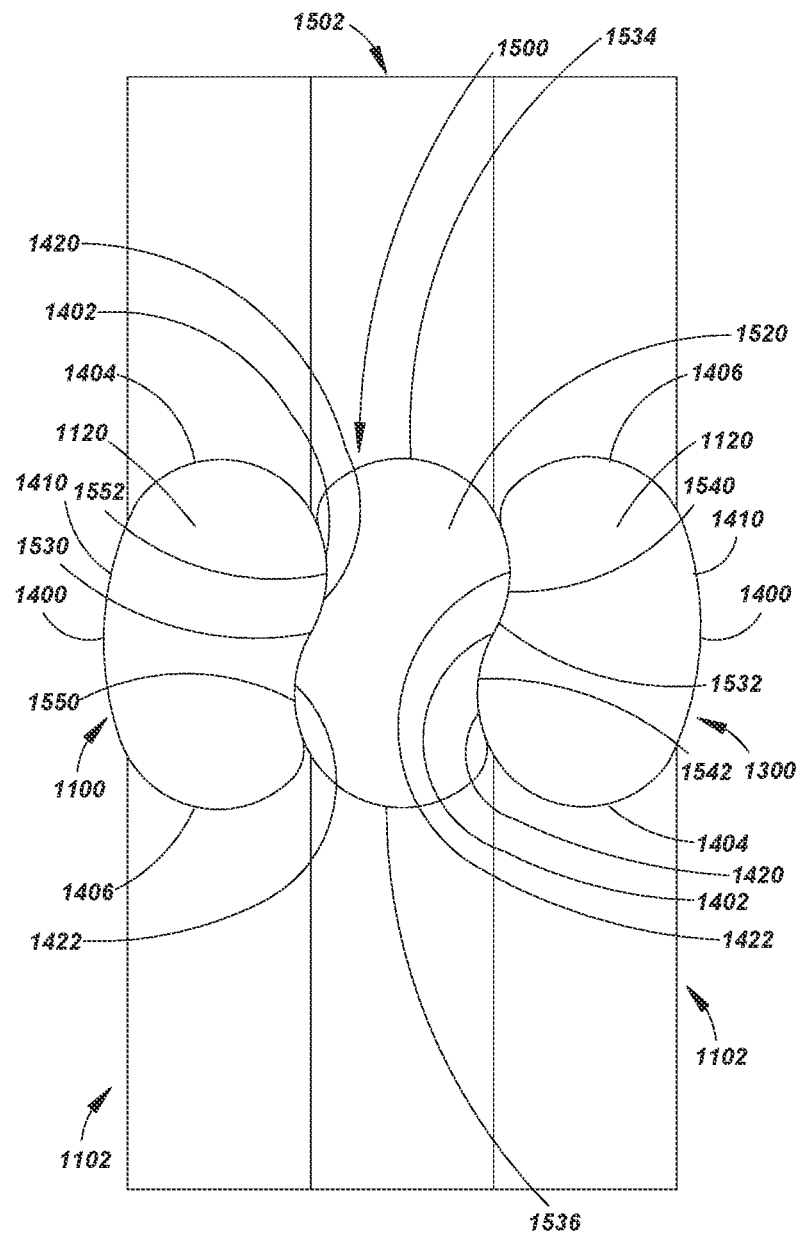
Figure 31:
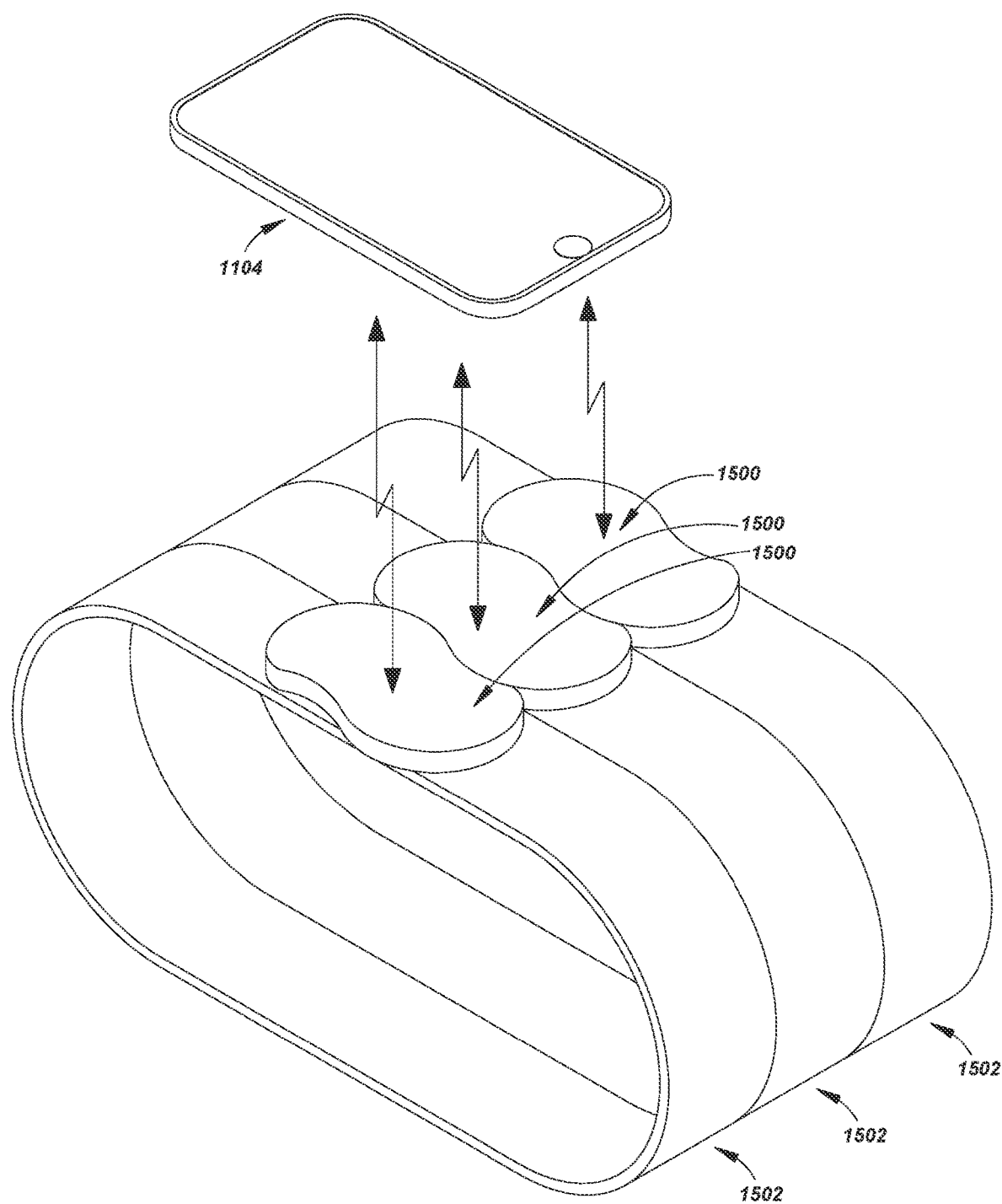
Figure 32:
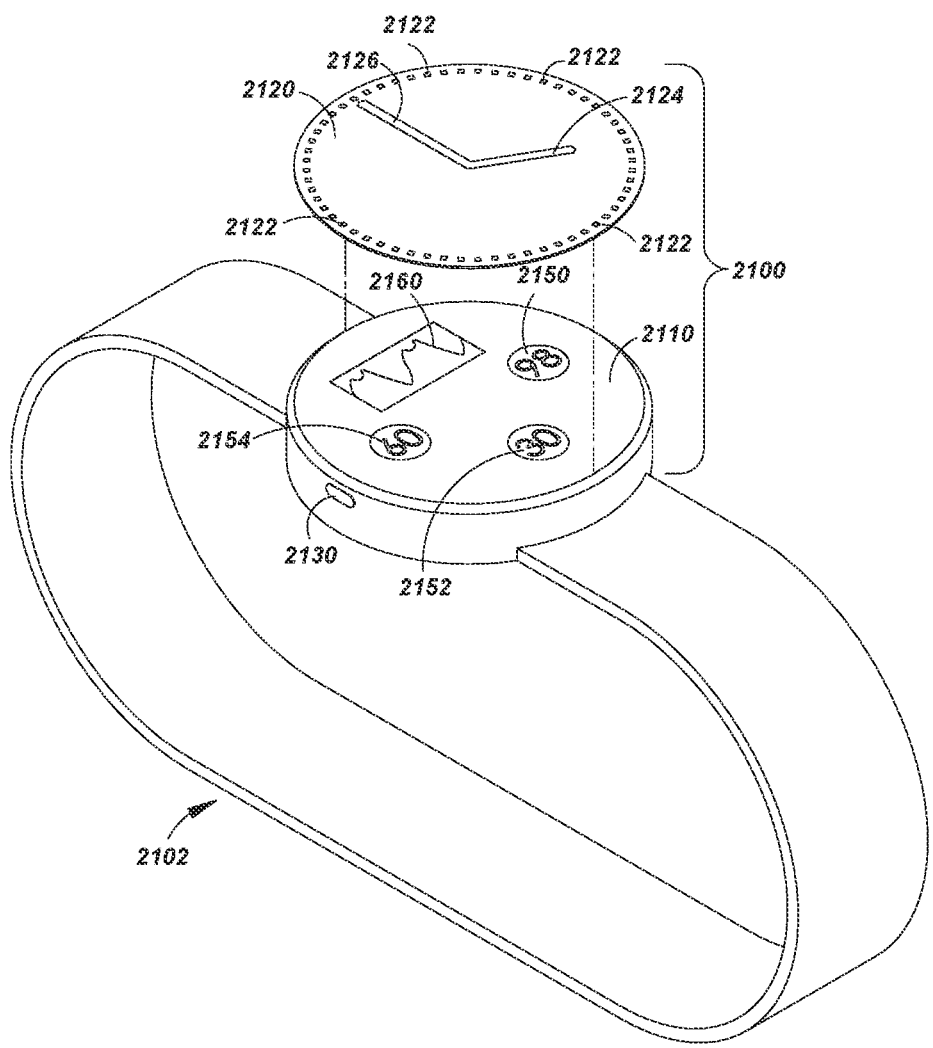
Figure 33:
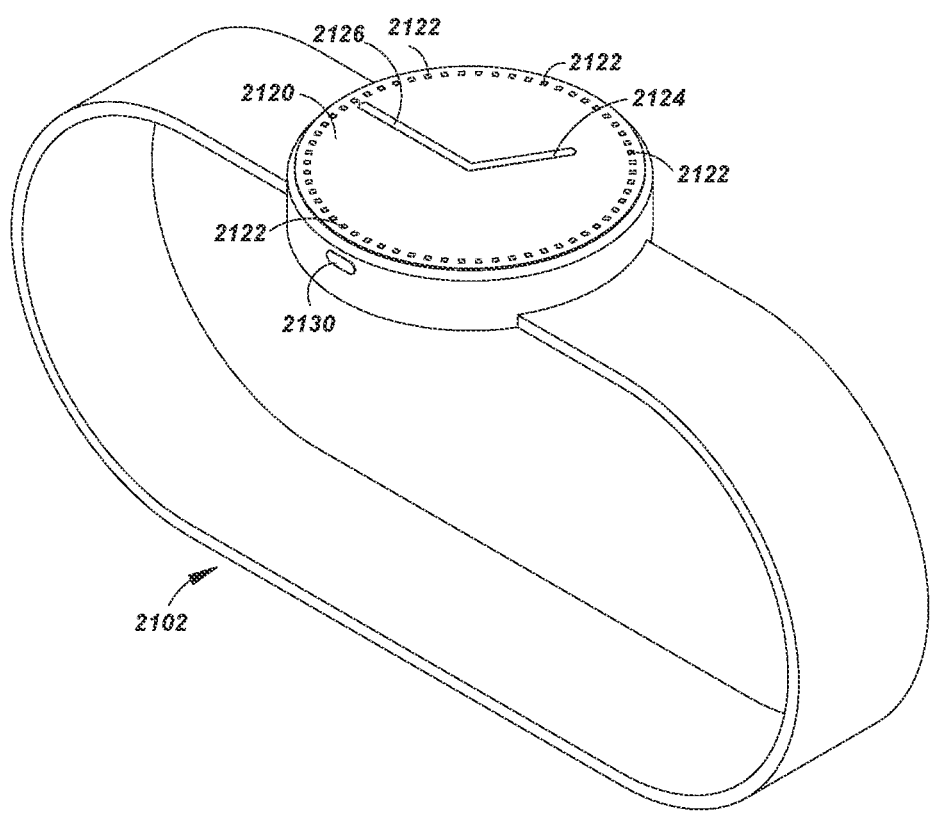
Figure 34:
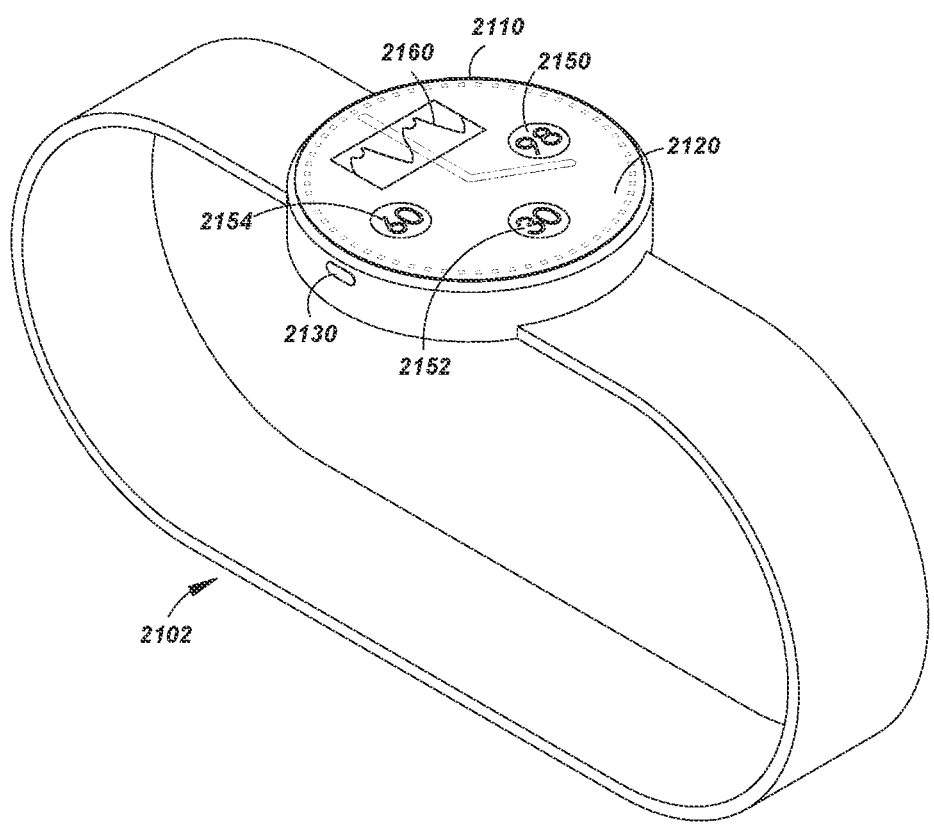

FIG. 7 illustrates a block diagram of the electronic circuitry of the smartwatch, which includes a first electronic subsystem in the lower base housing portion of the smartwatch, the first electronic subsystem powered by an auxiliary battery, the electronic circuitry of the smartwatch further including a second electronic subsystem in the upper removable housing portion of the smartwatch, the second electronic subsystem powered by a main battery, the electronic circuitry illustrated with the upper removable housing portion of the smartwatch attached to the lower base housing portion and with the first electronic subsystem receiving power from the second electronic subsystem;

FIG. 8 illustrates a block diagram of the second electronic subsystem separated from the first electronic subsystem when the upper removable housing portion of the smartwatch is detached from the lower base housing portion of the smartwatch, the electronic circuitry illustrated with the first electronic subsystem in wireless communication with the second electronic subsystem;

FIG. 9 illustrates an upper perspective view of an alternative embodiment of a smartwatch having a removable battery pack, the view in FIG. 9 showing the smartwatch and the removable battery pack prior to attachment of the removable battery pack to the smartwatch;

FIG. 10 illustrates a lower perspective view of the smartwatch and removable battery pack of FIG. 9;

FIG. 11 illustrates the removable battery pack of FIGS. 9 and 10 as viewed in FIG. 10 with the removable battery pack rotated to show electrodes on two of the attachment legs;

FIG. 12 illustrates the removable battery pack of FIGS. 9 and 10 rotated 180 degrees with respect to the view of FIG. 11 to show electrodes on the two other attachment legs;

FIG. 13 illustrates a bottom view of the smartwatch of FIGS. 9 and 10 showing the four electrodes on the smartwatch;

FIG. 14 illustrates an upper perspective view of the smartwatch and removable battery pack of FIGS. 9 and 10 showing the removable battery pack attached to the smartwatch;

FIG. 15 illustrates a top view of the smartwatch and removable battery pack showing the removable battery pack attached to the smartwatch as in FIG. 14;

FIG. 16 illustrates a lower perspective view of the smartwatch and the removable battery pack with the removable battery pack attached to the smartwatch as in FIG. 13;

FIG. 17 illustrates a bottom plan view of the smartwatch and the removable battery pack of FIG. 16 showing the attachment legs positioned over the electrodes of the smartwatch;

FIG. 18 illustrates a charging circuit and a battery within the smartwatch showing the connections to the removable battery pack via the external electrodes;

FIG. 19 illustrates an upper perspective view of a first fitness tracker attached to a band that enables the first fitness tracker to be attached to the limb (not shown) of a user, the fitness tracker communicating wirelessly to a smartphone;

FIG. 20 illustrates a lower perspective view of the first fitness tracker of FIG. 19 showing a sensor interface on a bottom surface of the fitness tracker;

FIG. 21 illustrates a simplified electronic circuit within the first fitness tracker of FIGS. 19 and 20, the electronic circuit coupled to a sensor;

FIG. 22 illustrates an alternative simplified electronic circuit within the first fitness tracker of FIGS. 19 and 20, the electronic circuit coupled to a motion tracking subsystem;

FIG. 23 illustrates an upper perspective view of a second fitness tracker having an enclosure configuration that engages with the enclosure configuration of the first fitness tracker of FIGS. 19 and 20, the second fitness tracker shown spaced apart from the first fitness tracker prior to engagement of the two fitness trackers;

FIG. 24 illustrates a top plan view of the first and second fitness trackers of FIG. 23 prior to engagement of the two fitness trackers;

FIG. 25 illustrates an upper perspective view of the first and second fitness trackers of FIGS. 23 and 24 positioned on a limb (not shown) of a user with the two fitness trackers positioned adjacent to each other with the upper portion of the second fitness tracker engaging the upper portion of the first fitness tracker;

FIG. 26 illustrates a top plan view of the first fitness tracker and the second fitness tracker with the two upper portions engaged as illustrated in FIG. 25;

FIG. 27 illustrates an upper perspective view of a third fitness tracker having an upper portion having a first selected contour on a first peripheral surface and having a second selected contour on a second peripheral surface;

FIG. 28 illustrates a top plan view of the third fitness tracker of FIG. 27;

FIG. 29 illustrates an upper perspective view of the third fitness tracker of FIGS. 27 and 28 positioned between the first fitness tracker of FIGS. 19 and 20 and the second fitness tracker of FIG. 23 with the upper portion of the third fitness tracker engaging the upper portions of the first fitness tracker and the second fitness tracker, each fitness tracker communicating wirelessly with a smartphone;

FIG. 30 illustrates a top plan view of the third fitness tracker positioned between the first and second fitness tracker as shown in FIG. 29;

FIG. 31 illustrates three fitness trackers wherein each of the three fitness trackers has an upper portion corresponding to the upper portion of the third fitness tracker of FIG. 29, the three fitness trackers positioned on a limb (not shown) of a user the upper portions of the three fitness trackers engaged, each of the three fitness trackers communicating wirelessly with a smartphone;

FIG. 32 illustrates an exploded upper perspective view of an embodiment of a smartwatch having an interactive screen display and an e-ink (e-paper) screen display, the exploded view illustrating the e-ink screen display prior to positioning the e-ink display over the interactive screen display;

FIG. 33 illustrates the smartwatch of FIG. 32 with the e-ink screen display installed as an overlay over the interactive display, the smartwatch shown in the analog watch display mode; and FIG. 34 illustrates the smartwatch of FIG. 33 with the e-ink screen display in the transparent mode such that the data and graphics information of the interactive screen display is visible through the e-ink screen display.

DESCRIPTION OF ILLUSTRATED EMBODIMENTS

As used throughout this specification, the words "upper," "lower," "longitudinal," "upward," "downward," "proximal," "distal," and other similar directional words are used with respect to the views being described.

Physiological parameter sensors are particularly useful in monitoring a user while the user is sleeping to determine whether the user is experiencing unusual conditions that may indicate a medical condition (e.g., sleep apnea) that should be evaluated.

Although decreasing size and decreasing power consumption of digital and analog electronics allows the number of functions performed by a smartwatch to increase, the electronics must be powered by a battery, and the battery must be charged to maintain the available power. A smartwatch may be charged using a wired interconnection to a charging source or by using a magnetic induction charger. In either case, the smartwatch is effectively "tethered" to the charger during the charging process. Such charging generally requires the user to remove the smartwatch to connect the smartwatch to a charging cord or to a magnetic induction charger. In either case, the smartwatch is no longer able to monitor the user's position and orientation or able to monitor the user's physiological parameters while the smartwatch is being charged. If, for example, the user chooses to charge the smartwatch at night when the user is less likely to use the smartphone connection features of the smartwatch, the smartwatch is no longer monitoring the user's physiological parameter while the user is sleeping. Accordingly, changes in the parameters that occur when the user is charging the smartwatch might be missed.

Figure 1:
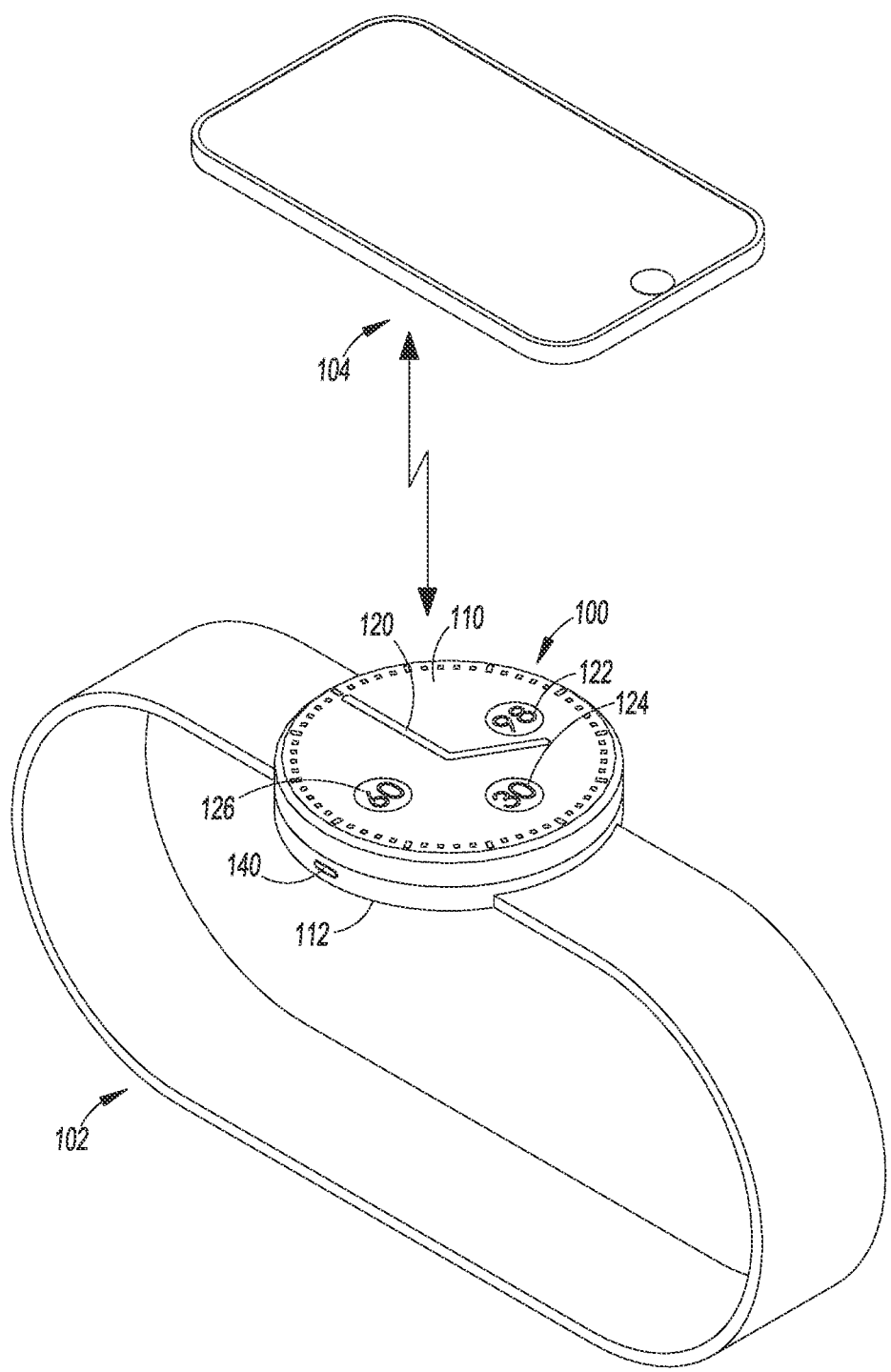
FIG. 1 illustrates an upper perspective view of a smartwatch showing a plurality of visual displays on an upper surface, wherein the upper surface also provides a tactile (touch sensitive) interface.
Figure 2:
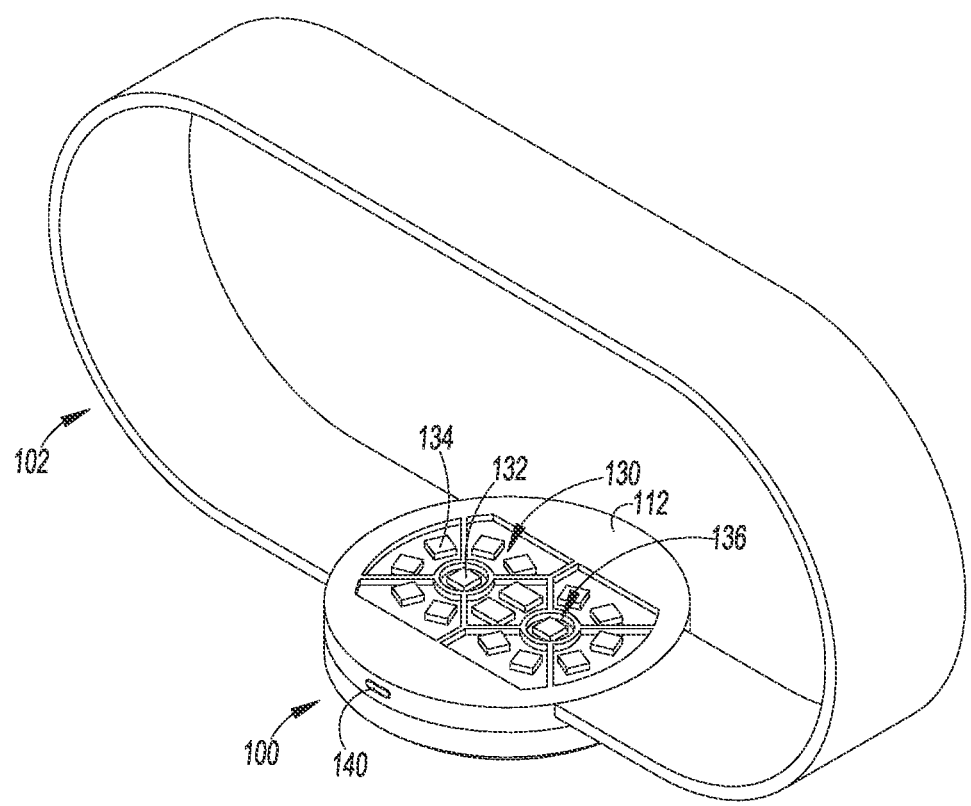
FIG. 2 illustrates a lower perspective view of the smartwatch of FIG. 1 showing sensor interfaces on a bottom surface of the smartwatch.

FIG. 1 illustrates an upper perspective view of a smartwatch 100 attached to a wristband 102. The wristband allows a user (not shown) to secure the smartwatch to a portion of a limb, such as the wrist of the user. The smartwatch may be in wireless communication with a smartphone 104 or another interactive device. FIG. 2 illustrates a lower perspective view of the smartwatch of FIG. 1.

The smartwatch 100 has an upper surface 110 and a lower surface 112. When the smartwatch is secured to the limb portion of the user using the wristband 102, the lower surface of the smartwatch contacts the skin of the limb portion. The upper surface of the smartwatch is configured as an interactive display and tactile (touch sensitive) input device. Such surfaces are well known in the art and are not described in detail herein. An example of a display is shown in FIG. 1 wherein a first portion 120 of the display represents the dial and the hands of an analog watch; a second portion 122 of the display provides a numeric representation of a first physiological parameter (e.g., the temperature) of the user wearing the smartwatch; a third portion 124 of the display provides a numeric display of a second physiological parameter (e.g., the heartrate) of the user, and a fourth portion 126 of the display provides a numeric representation of a third physiological parameter of the user. The dial and hands of the watch and the three numeric displays visual displays on a liquid crystal display (LCD) screen or other display device. The display device may be reconfigured to represent different information (e.g., the numeric dialing pad of a telephone, a text messaging screen or the like).

As is known in the art, the information displayed on the upper surface 110 of the smartwatch 100 changes in accordance with the operational mode of the smartwatch. The operational mode may be changed by the user or changed automatically as determined by events detected by the smartwatch. For example, the user may select a mode in which the smartwatch operates as a remote input/output device for the smartphone 104, and the upper surface displays information related to the smartphone interface (e.g., the display is configured as a numeric dialing pad or configured as a text messaging screen). The smartwatch may detect a change in a sensed physiological parameter and may automatically display detailed information regarding the sensed parameter. In many cases, the upper surface displays icons in areas of the upper surface that the user can touch to provide inputs to the smartwatch (e.g., touching the area of a number of a displayed numeric dialing pad causes the smartwatch to send a signal to the smartphone as part of a command to the smartphone).

As illustrated in FIG. 2, the lower surface 112 of the smartwatch 100 can include one or more sensors that interact with the skin of the user's wrist to obtain physiological parameters indicative of the physical condition of the user. The lower surface can include one or more of a temperature sensor, a bioimpedance sensor, a blood oxygenation sensor, an electrocardiogram (ECG) sensor or the like. For example, an oxygen saturation (SpO2) sensor 130 is illustrated with a central light source (e.g., a light-emitting diode (LED)) 132 surrounded by a plurality of photodetectors 134. The light emitted by the LED is sensed by the photodetectors and is processed within the smartwatch to determine a percentage of oxygen saturation. A second sensor 136 may also be provided with a similar structure to the first sensor or with a different structure.

The smartwatch 100 can also include at least one mechanical pushbutton (mode switch) 140 positioned on peripheral surfaces of the watch. The mechanical pushbuttons may be activated, for example, to turn off and turn on the displays of the upper surface 110, to change operational modes, or to initiate or control other options. In some cases, the mode switch 140 can act as a privacy switch. That is, activating the mode switch 140 can cause the one or more sensors of the smartwatch 100 to at least momentarily stop sensing physiological parameters of the user and/or cause the display of the smartwatch 100 to at least momentarily stop displaying information indicative of at least one physiological parameter of the user.

Figure 3:
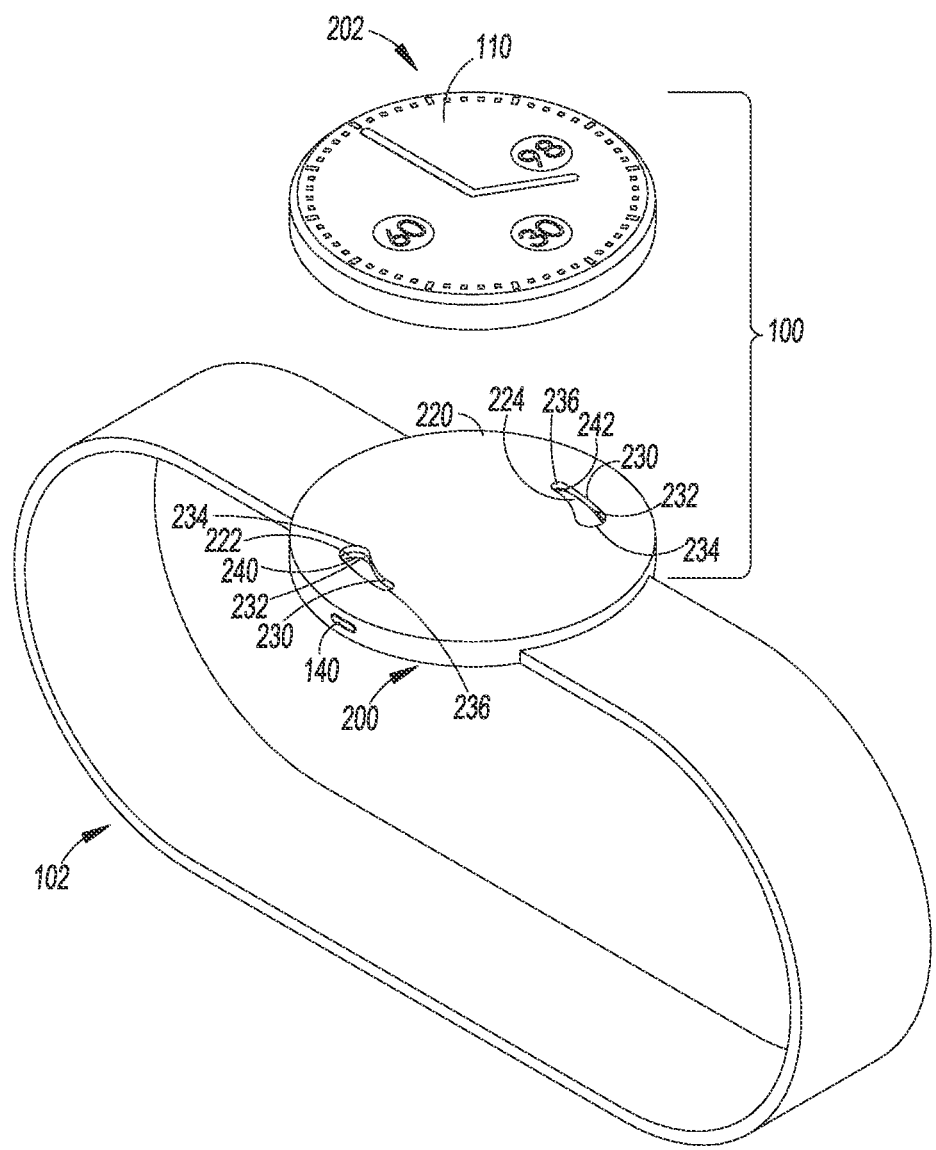
FIG. 3 illustrates an upper exploded perspective view of the smartwatch of FIGS. 1 and 2 showing the smartwatch separated into a first (lower base) portion and a second (upper removable) portion.
Figure 4:
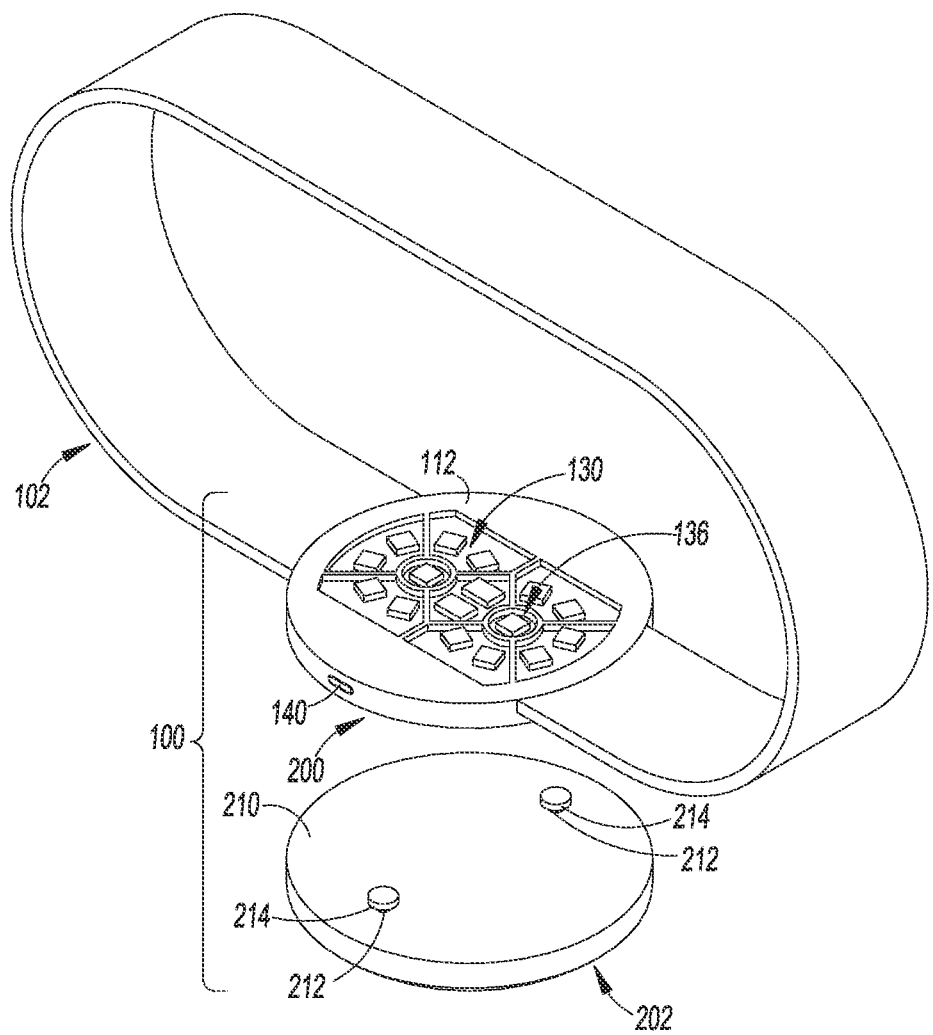
FIG. 4 illustrates a lower exploded view of the smartwatch of FIGS. 1 and 2 showing the lower surface of the upper removable housing portion of the smartwatch.

Generally, a smartwatch includes a single housing unit having the upper surface 110 and the lower surface 112; however, in the illustrated embodiment, the smartwatch 100 of FIGS. 1 and 2 can include a first housing portion 200 and a second housing portion 202, which are shown in the upper perspective exploded view of FIG. 3 and the lower perspective exploded view of FIG. 4. In some cases, the first housing portion does not include a display. The first housing portion may also be referred to herein as the lower housing portion, the base housing portion or the base portion. The second housing portion may also be referred to herein as the upper housing portion, the removable housing portion or the removable portion. The base (lower) housing portion is attached to the wristband 102 as described above. The removable (upper) housing portion is removably attached to the base housing portion such that the removable housing portion can be easily attached to and easily removed from the base housing portion as described below.

Various attachment techniques may be used to removably attach the removable housing portion 202 to the base housing portion 200 of the smartwatch 100. For example, in the illustrated embodiment, a lower surface 210 of the removable housing portion (see FIG. 4) can include two engagement posts 212 that extend perpendicularly from the lower surface and which can include respective enlarged end portions 214. The engagement posts are spaced apart diametrically with respect to center of the lower surface.

An upper surface 220 of the base (lower) housing portion 200 can include a first arcuate slot 222 and a second arcuate slot 224. The arcuate slots are spaced apart by a distance corresponding to the spacing of the engagement posts. Each arcuate slot has an upper portion 230 and a lower portion 232. The upper portion of each slot has respective first enlarged end opening 234 that is sized to receive the enlarged end portion of one of the engagement posts. The upper portion of each slot has a respective second narrower end opening 236. The lower portion of each slot has a continuous arcuate width. A first end 240 of the lower portion of each slot (see the first arcuate slot 222) has the same size as the first enlarged end opening of the upper portion of the slot. A second end 242 of the lower portion of each slot (see the second arcuate slot 224) also has the same size as the first end of the lower portion of the slot.

The removable housing portion 202 is attached to the base housing portion 200 by aligning the enlarged end portions 214 of the engagement posts 212 with the first enlarged end openings 234 of the arcuate slots 222. The enlarged end portions are inserted into the enlarged openings until the lower surface 210 of the removable housing portion is flush with the upper surface 220 of the base housing portion. The removable housing portion is rotated (e.g., approximately 30 degrees counterclockwise) until each engagement post is positioned against the respective second narrower end opening 236 of the upper portion 230 of each respective arcuate slot.

When positioned in the described manner, the enlarged end portions 214 of the engagement posts 212 are positioned below the narrower second end openings 236 of the upper portions 230 of the arcuate slots 222, 224. The enlarged end portions of the engagement posts are precluded from moving vertically. Thus, the lower surface 210 of the removable housing portion 202 is secured tightly against the upper surface 220 of the base housing portion 200. The tight fit and the resulting friction between the two surfaces prevents the removable housing portion from being removed from the base housing portion without deliberate effort by the user. To remove the removable housing portion from the base housing portion, the user rotates the removable housing portion in the opposite direction (e.g., clockwise) to realign the enlarged end portions of the engagement posts with the first ends of the arcuate slots such that the enlarged end portions can be extracted from the arcuate slots.

Other techniques (not shown) may also be used to removably secure the removable housing portion 202 to the base housing portion 200. For example, the two housing portions may be magnetically coupled. The two housing portions may be engaged with respective threads around the perimeter of each housing portion. Tabs and engagement surfaces may be provided on the two housing portions to enable the two portions to be snapped together.

Figure 5:
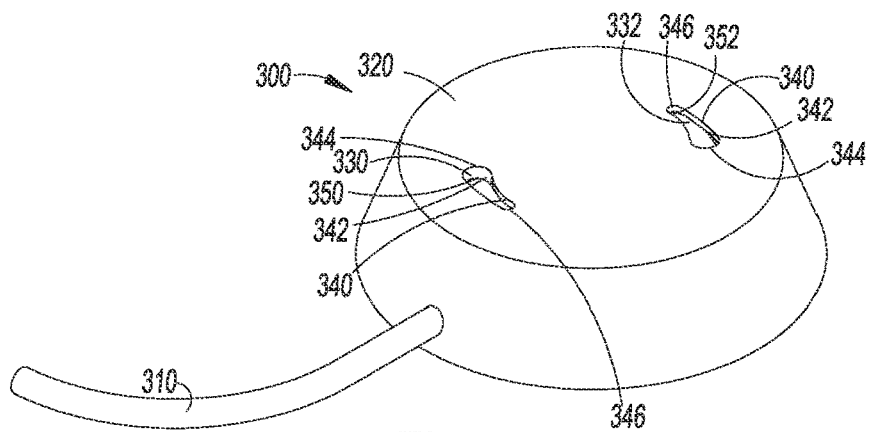
FIG. 5 illustrates a perspective view of an exemplary charging unit.

Removing the removable housing portion 202 from the base housing portion 200 of the smartwatch 100 enables the user to position the removable housing portion in communication with a charging source without removing the base housing portion from the user's wrist. FIG. 5 illustrates a charging unit 300 suitable for charging the removable housing portion of the smartwatch. The charging unit receives power via a power cable 310, which may be connected to a wall adapter (not shown) or to a USB port (not shown).

Figure 6:
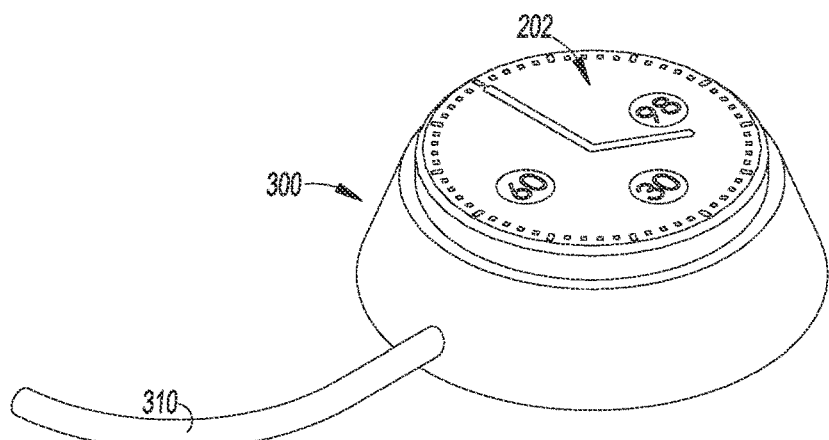
FIG. 6 illustrates the upper removable housing portion of the smartwatch of FIGS. 1 and 2 positioned on a charging unit and illustrates the lower base housing portion of the smartwatch displaced from the upper removable housing portion.
Figure 6:
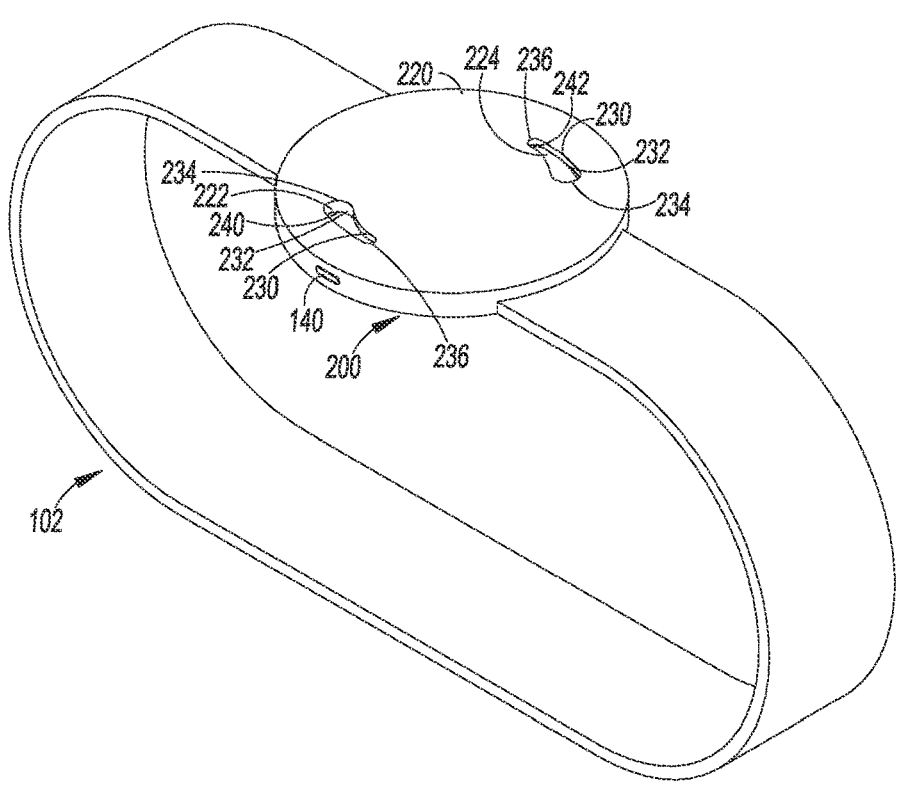

The charging unit 300 has a flat upper surface 320 (FIG. 5) that receives the removable housing portion 202 as shown in FIG. 6. In the illustrated embodiment, the upper surface of the charging unit can include a first arcuate slot 330 and a diametrically opposed second arcuate slot 332. The two arcuate slots are similar to the arcuate slots 222, 224 of the upper surface 220 of the base housing portion 200 (see FIG. 3). The arcuate slots of the charging unit are spaced apart by a corresponding distance as the arcuate slots of the base housing portion.

Each arcuate slot 330, 332 has an upper portion 340 and a lower portion 342. The upper portion of each slot has respective first enlarged end opening 344 that is sized to receive the enlarged end portion of one of the engagement posts. The upper portion of each slot has a respective second narrower second end opening 346. The lower portion of each slot has a continuous arcuate width. A first end 350 of the lower portion of each slot (see the first arcuate slot 330) has the same size as the enlarged upper end opening. A second end 352 of the lower portion of each slot (see the second arcuate slot 332) also has the same size as the first end of the lower portion of the slot.

The removable housing portion 202 of the smartwatch 100 is coupled to the charging unit 300 by positioning the lower surface 210 of the removable housing portion over the upper surface 320 of the charging unit with the enlarged end portion 214 of each engagement post 212 aligned with a respective first enlarged end opening 344 of the arcuate slots 330, 332 of the upper surface of the charging unit. The enlarged end portions of the engagement posts are inserted into the enlarged first ends of the arcuate slots. The removable housing portion is then rotated (e.g., approximately 30 degrees counterclockwise) to secure the removable housing portion to the charging unit.

The charging unit 300 operates to magnetically couple electrical energy to the removable housing portion 202 in a conventional manner. Alternatively, the arcuate slots 330, 332 may also be metalized electrodes and the engagement posts 212 of the removable housing portion 202 may be metalized electrodes so that the charging unit may couple electrical energy to the removable housing portion by electrical conduction. After charging is completed, the removable housing portion is removed from the charging unit by rotating the removable housing portion in the opposite direction (e.g., clockwise).

In further alternative embodiments, the removable housing portion 202 of the smartwatch 100 may not have the illustrated engagement posts 212. The charging unit 300 may have an outer peripheral raised rim (not shown) that centers the removable housing portion on the charging unit to assure alignment of the magnetic field generated by the charging unit with the magnetic receiving unit within the removable housing portion.

FIG. 6 illustrates the removable housing portion 202 of the smartwatch 100 positioned on the charging source 300 while the base housing portion 200 remains secured to the wristband 102 so that the lower portion can remain in contact with the user's wrist (not shown). Accordingly, the user is free to move about without being tethered to the charger.

Although the removable housing portion 202 of the smartwatch 100 is positioned on the charging unit 300 and is physically separated from the base housing portion 200 in FIG. 6, the smartwatch retains a substantial portion of the functionality of the smartwatch. This continued functionality is provided by parsing the electronics of the smartwatch into at least first electronic subsystem 400 and a second electronic subsystem 402 as illustrated in FIG. 7. The first electronic subsystem can include the electronics housed within the base (lower) housing portion. The second electronic subsystem can include the electronics housed within the removable (upper) housing portion. The second electronic subsystem is coupled to the upper surface 110 of the smartwatch 100, which functions as a display and tactile display interface. The parsing of the first and second electronic subsystems in FIG. 7 is only one example of the parsing of the overall electronics into the two subsystems. Some of the electronic components shown in one of the two subsystems may be moved to the other subsystem. Some of the electronic components shown in one of the two subsystems may also be duplicated in the other subsystem.

In the example of FIG. 7, the second (upper) electronic subsystem 402 can include an input/display electronics subsystem 410 that interacts with the interactive display and tactile (touch sensitive) upper surface 110. The input/display electronic subsystem may also interact with an audio output (e.g., a piezoelectric speaker) 414 and an audio input (microphone) 416.

The second electronic subsystem 402 can also include at least one remote wireless communication interface 420 that enables the second electronic subsystem to communicate with the smartphone 104 (FIG. 1) or another remote device. For example, the wireless communication interface may be a Bluetooth® interface. The wireless communication interface can also include a WiFi interface. The second electronic subsystem can also include a dedicated local wireless interface 426 to the first electronic subsystem 400. In the illustrated embodiment, the dedicated local interface to the first electronic subsystem is a second wireless communication (local) interface, such as a Bluetooth® low energy (BLE). The two wireless interfaces may be two components of a single wireless interface.

The second electronic subsystem 402 can also include a second electronic subsystem processor 430 that communicates with the input/display electronics subsystem 410 and the wireless communication interface 420 in a conventional manner. The second electronic subsystem processor is programmed to interact with the display and inputs of the upper surface 110, to perform routines in response to user commands, to monitor sensory information from the second electronic subsystem 402 and to communicate with the smartphone 104 (FIG. 1) or other remote devices.

The second electronic subsystem 402 can also include a main battery 440 and a battery charging system 442 and an upper housing voltage generator 444. In the illustrated embodiment, the battery charging system converts magnetic energy from a built-in antenna 446 to a DC voltage for charging the battery. The main battery provides one or more DC voltages to the components within the second electronic subsystem via the upper housing voltage generator. The upper housing voltage generator provides at least one DC voltage output to the first electronic subsystem 400 via the engagement posts 212 as described below. The battery charging system is couplable to an external source of power to receive energy and to convert the energy to suitable voltage to charge the main battery. For example, in the illustrated embodiment, the battery charging system is couplable to the magnetic induction charging unit 300 as shown in FIG. 5 and as is described below with respect to FIG. 8. The battery charging system receives electromagnetic energy from the charger and converts the electromagnetic energy to a suitable DC electric current to charge the main battery. In other embodiments, the battery charging system can include a DC voltage input that receives DC electric current, which is converted to a suitable DC electric current to charge the main battery. For example, the engagement posts 212 may provide an input voltage to the voltage generator that can be used for charging the main battery. Magnetic induction charging and DC electric current charging are well known to the art.

As further illustrated in FIG. 7, the first electronic subsystem 400, which is housed in the base (lower) housing portion 200, can include a first electronic subsystem processor 500, a sensor interface 510, a wireless communication interface 520 and an auxiliary battery 530. The auxiliary battery provides one or more DC voltages to the components in the first electronic subsystem via a lower housing voltage generator 540. The first electronic subsystem processor is coupled to the mode switch 140. The first electronic subsystem can include a piezoelectric buzzer (alert device) 550 or other perceptible alert system. The perceptible alert system notifies the user of an incoming message or other alert.

The auxiliary battery receives power from the second electronic subsystem 402 via a power input interface 560. The power input interface is coupled to the first arcuate slot 222 and the second arcuate slot 224. When the base housing portion 200 is attached to the removable housing portion 202 as shown in FIG. 1, electrical energy from the upper housing voltage generator 444 in the second electronic subsystem 402 is electrically coupled to the arcuate slots via the engagement posts 212 of the base housing portion 200 to thereby provide electrical energy to the power input interface to charge the auxiliary battery. In alternative embodiments, separate pairs of electrodes may be provided on the removable housing portion and the base housing portion to provide charging current from the removable housing portion to the auxiliary battery in the base housing portion.

In the illustrated embodiment, the lower housing voltage generator 542 receives electrical energy from the auxiliary battery 530. When the removable housing portion 202 is attached to the base housing portion 200, the battery is charged and is then maintained fully charged from the electrical energy from the removable housing portion. The auxiliary battery provides electrical energy to the lower housing voltage generator. When the removable housing portion is removed from the base housing portion, the auxiliary battery continues to provide electrical energy to the first electronic subsystem.

In an alternative embodiment (not shown), the lower housing voltage generator 542 may receive electrical energy directly from the removable housing portion 202 when the removable housing portion is attached to the base housing portion. The auxiliary battery may only provide electrical energy to the base housing portion when the removable housing portion is detached as described below. In such an embodiment, diodes (not shown) can be included to assure that the auxiliary battery is only providing power to the first electronic subsystem 400 when the removable housing portion is detached from the base housing portion.

As shown in FIG. 7, the first electronic subsystem 400 in the base housing portion 200 communicates with the second electronic subsystem 402 in the removable housing portion 202 via the wireless communication interface 520 in the first electronic subsystem communicating with the local wireless interface 426 of the second electronic subsystem. The first electronic subsystem receives data and commands from the second electronic subsystem and transmits processed sensor information to the second electronic subsystem.

FIG. 8 illustrates a block diagram of the first electronic subsystem 400 separated from the second electronic subsystem 402 when the upper removable housing portion 202 of the smartwatch 100 is detached from the lower base housing portion 200 as shown in FIG. 6. The electronic circuitry illustrated with the first electronic subsystem remains in wireless communication with the second electronic subsystem via the wireless communication interface 520 communicating the local wireless interface 426. The auxiliary battery 530 within the first electronic subsystem is no longer receiving power from the second electronic subsystem because the engagement posts 212 are no longer engaged with the arcuate slots 222, 224. The absence of power being received by the power input interface 560 may be communicated to the first electronic subsystem processor 500 to cause the first electronic subsystem processor to enter a low power operating mode. For example, the first electronic subsystem processor may access the sensors 130, 136 at a lower repetition rate to conserve power. The first electronic processor may only activate the wireless communication interface 520 to communicate detected abnormalities or other changes instead of communicating continuous readings to the second electronic subsystem. When the upper removable housing portion is directly coupled to the lower base housing portion, the user may use the tactile input and display features of the upper surface 110 to select the sensing features to remain active when the upper removable housing portion is detached and the lower base housing portion is in the lower power mode.

If an abnormality or other warning occurs while the removable housing portion 202 is disconnected from the base housing portion 200, the user may receive a warning via the alert device 550. The user may also receive an alert via a haptic feedback that can be included in the base housing portion 200. Accordingly, the user is able to monitor selected physiological parameters while the main battery 440 in the second electronic subsystem is charging. If an alert occurs, the user can quickly detach the removable housing portion from the charging unit 300, reattach the two housing portions, and resume monitoring of physiological parameters using the full capabilities of the smartwatch 100.

FIGS. 9-18 illustrate an alternative embodiment that allows a smartwatch 600 to be charged while the user is wearing the watch. The smartwatch is attached to a wristband 602, which is shown partially broken away in the drawings. As described below, the smartwatch is chargeable using a magnetic charger, such as the charging unit 300 described above with respect to FIG. 5. As further described below, the smartwatch is also chargeable from a removable battery pack 610, which is shown separate from the smartwatch in FIGS. 9-13, and which is shown attached to the smartwatch in FIGS. 14-17.

As shown in FIG. 9, the smartwatch 600 can include an upper surface 620, a lower surface 630, and a peripheral wall 640. The peripheral wall extends between the upper surface and the lower surface.

The upper surface 620 of the smartwatch 600 may correspond to the upper surface 110 of the previously described smartwatch 100. As previously described, the upper surface provides an interactive display 650, which may display time of day and other information. The interactive display may also function as an input/output device.

The lower surface 630 of the smartwatch 600 encloses a conventional magnetic coupling system (see FIG. 18), which is positioned in the body of the smartwatch proximate to a circular area 652 of the lower surface. The circular area of the lower surface of the smartwatch may be placed on the charging unit 300 (FIG. 5) to charge the smartwatch in a conventional manner.

The peripheral wall 640 of the smartwatch 600 can include a middle wall portion 660, which extends for a selected distance generally midway between the upper surface 620 and the lower surface 630. The middle wall portion forms the largest circumference of the smartwatch. The peripheral wall can further include an upper wall portion 670, which slopes inwardly from the middle wall portion and extends to the upper surface 620. In the illustrated embodiment, at least a portion 672 of the upper wall portion is frustoconical.

The peripheral wall 640 can further include a lower wall portion 680, which slopes inwardly from the middle wall portion 660 to the lower surface 630. In the illustrated embodiment, at least a portion 682 of the lower wall portion is frustoconical.

The smartwatch 600 can include a first control device 690 extending from the middle portion 660 of the peripheral wall 640 of the smartwatch and can include a second control device 692 extending from the middle portion of the peripheral wall of the smartwatch. In the illustrated embodiment, the two control devices are diametrically opposed from each other on opposite sides of the smartwatch; however, the control devices may be located elsewhere about the peripheral wall. In the illustrated embodiment, the first control device is a wheel, which may be rotated to move among items on the interactive display 650 of the upper surface 620. In the illustrated embodiment, the second control device is a pushbutton, which may be used, for example, to activate and deactivate the display and to select functions (e.g., modes) of the smartwatch. Additional controls or fewer controls can be included in accordance with the functionality of the smartwatch.

The smartwatch 600 can include a plurality of electrodes on the frustoconical portion 682 of the inwardly sloped lower wall portion 680. In the illustrated embodiment, the smartwatch can include a first electrode 700, a second electrode 702, a third electrode 704 and a fourth electrode 706. In alternative embodiments, the smartwatch can include only two electrodes. In the illustrated embodiment, the four electrodes are spaced apart angularly by approximately 45 degrees. The electrodes are connected to an internal battery charging circuit (battery charger) 710, which is illustrated in FIG. 18. As further illustrated in FIG. 18, the battery charging circuit also receives charging energy from an antenna (e.g., a coil) 712 positioned proximate to the circular area 652 of the lower surface 630 of the smartwatch. Only two of the four electrodes are needed to provide electrical energy to the charging circuit. In the illustrated embodiment, the first electrode and the third electrode are interconnected to provide a relatively positive voltage to the charging circuit, and the second electrode and the fourth electrode are interconnected to provide a relatively negative voltage. In alternative embodiments, only two electrodes may be used to provide the charging voltage, and the other two electrodes may be used to communicate between the removable battery pack 610 and the smartwatch. The removable battery pack 610 can also be referred to as a removable housing. In some cases, the battery pack 610 does not include a display.

In the illustrated embodiment, each of the four electrodes 700, 702, 704, 706 is circular; however, the electrodes may have different sizes and shapes. The electrodes can include conventional material such as copper or copper with gold or silver plating.

In the illustrated embodiment, the removable battery pack 610 can include an upper body portion 750. The upper body portion has the shape of a rectangular parallelepiped in the illustrated embodiment; however, other shapes may also be used. The width of the removable battery pack is selected such that when the removable battery pack is positioned on the smartwatch as shown in FIGS. 14-17, a portion of the smartwatch extends beyond the sides of the removable battery pack so that the first control 690 and the second control 692 are accessible.

The upper body portion 750 of the removable battery pack 610 encloses a battery (not shown) and electronic circuitry (not shown) that controls the charging and discharging of the battery within the removable battery pack.

The upper body portion 750 of the removable battery pack 610 has an upper surface 760 and a lower surface 762. The upper surface of the upper body portion can include a circular portion 780. In some cases, the circular portion 780 can include an opening along an upper surface 760 of the battery pack 610. The opening along the upper surface 760 of the battery pack 610 can permit visualization of the interactive display 650 when the battery pack 610 is attached to the smartwatch 600. Beneficially, this can allow users to visualize the interactive display 650 while the battery pack 610 is attached to the smartwatch 600. An internal antenna (e.g., coil) is positioned within the upper body portion proximate to the circular portion. The removable battery pack is charged by positioning the removable battery pack on a charging unit, such as the charging unit 300 of FIG. 5, with the circular portion of the upper surface of the removable battery pack proximate to the top surface of the charging unit. The removable battery pack is charged in a conventional manner.

The lower surface 762 of the upper body portion 750 of the removable battery pack 610 is flat in the illustrated embodiment. A first lower attachment portion 800 extends from one end of the lower surface, and a second lower attachment portion 810 extends from an opposite end of the lower surface. The first lower attachment portion can include a first inner surface 802. The second lower attachment portion can include a second inner surface 812. The first and second inner surfaces are sized and shaped to conform to the contours of the upper wall portion 670 of the smartwatch 600. Accordingly, when the removable battery pack is positioned over the smartwatch as shown in FIGS. 14-17, the lower surface of the upper body portion of the removable battery pack rests against the upper surface 620 of the smartwatch, and the first and second inner surfaces rest against respective portions of the upper wall portion 670 of the smartwatch.

The first attachment portion 800 has a first attachment leg 820 extending from a first side and has a second attachment leg 822 extending from a second side. Similarly, the second attachment portion 810 has a third attachment leg 824 extending from a first side and has a fourth attachment leg 826 extending from a second side. Each of the four attachment legs curves inwardly toward the center of the removable battery pack.

The first attachment leg 820 has a first attachment leg inner surface 830 (FIG. 12). The second attachment leg 822 has a second attachment leg inner surface 832 (FIG. 12). The third attachment leg 824 has a third attachment leg inner surface 834 (FIG. 11). The fourth attachment leg 826 has a fourth attachment leg inner surface 836. The four attachment legs are configured so that the respective inner surfaces conform to the middle wall portion 660 and the lower wall portion 680 of the smartwatch 600. The four attachment legs are resilient such that when the removable battery pack 610 is positioned over the smartwatch, the four attachment legs flex to allow the attachment legs to expand outwardly to pass over the larger diameter middle wall portion of the smartwatch. When the lower surface 762 of the removable battery pack is positioned against the upper surface 620 of the smartwatch, the resilience of each of the four attachment legs causes the respective inner surface of each attachment leg to press against a corresponding portion of the frustoconical portion 682 of the lower wall portion 680 of the smartwatch as shown in FIGS. 14, 16 and 17.

As shown in FIG. 12, the first attachment leg inner surface 830 of the removable battery pack 610 has a first battery pack electrode 850 positioned thereon. The second attachment leg inner surface 832 has a second battery pack electrode 852 positioned thereon. As shown in FIG. 11, the third attachment leg inner surface 834 of the removable battery pack has a third battery pack electrode 854 positioned thereon. The fourth attachment leg inner surface 836 has a fourth battery pack electrode 856 positioned thereon. When the removable battery pack is secured to the smartwatch 600 as illustrated in FIGS. 14-17, the resilience of each attachment leg 820, 822, 824, 826 provides sufficient pressure to force each battery pack electrode against a respective one of the smartwatch electrodes 700, 702, 704, 706 to provide electrical contact between the electrodes. The removable battery pack can also include temperature monitoring sensor to monitor overheating during the charging.

In the illustrated embodiment, the first, second, third and fourth battery pack electrodes 850, 852, 854, 856 of the removable battery pack 610 are sized and shaped to engage the first, second, third and fourth electrodes 700, 702, 704, 706, respectively, of the smartwatch 600. For example, the removable battery pack electrodes are illustrated as circular electrodes in FIGS. 11 and 12 having sizes similar to the sizes of the smartwatch electrodes. In alternative embodiments, the four battery pack electrode may have sizes and shapes that differ from the smartwatch electrodes. For example, the removable battery pack electrodes may be larger than the smartwatch electrodes to accommodate tolerance in the fit of the removable battery pack with the smartwatch. In one example (not shown), the removable battery pack electrodes can include rectangular bands that extend at least partially across the respective inner surfaces 830, 832, 834, 836 of the attachment legs 820, 822, 824, 826. In some embodiments, only two electrodes are included on the smartwatch 600 for charging. Further, the removable battery pack may also have only two electrodes that correspond to the smartwatch electrodes. In some instances, the removable battery pack 610 can include four electrodes, but the smartwatch 600 can only include two electrodes so that the removable battery pack 610 can be placed in any orientation on the smartwatch 600 as long as the two electrodes on both components are in contact.

As shown in a block diagram 900 of FIG. 18, the internal battery charging system of the smartwatch 600 can include an internal battery 910 and the battery charger 710. The charging system receives electrical energy from the antenna (e.g., coil) 712 to enable the battery within the smartwatch to be charged using a magnetically coupled charger such as the charging unit 300 (FIG. 5). The charging system is also electrically connected to the four electrodes 850, 852, 854, 856 to enable the battery to be charged from the removable battery pack 610. In the illustrated embodiment, the first electrode 850 is electrically connected to the third electrode 854 to receive a relatively positive voltage (e.g., +), and the second electrode 852 is electrically connected to a relatively negative voltage (e.g., —). By connecting the pairs of electrodes in this manner, the removable battery pack can be positioned on the smartwatch as shown or rotated by 180 degrees to provide the correct voltage polarity to the smartwatch.

When the removable battery pack 610 is attached to the smartwatch 600 as shown in FIGS. 13-17, the internal battery 910 is charged from the removable battery pack. The smartwatch remains fully operable to monitor the physiological parameters as described above. If the wearer of the smartwatch receives an alert as the result of the physiological monitoring or for other reasons (e.g., an incoming call or text message), the wearer can quickly remove the removable battery pack from the smartwatch and have complete access to the interface 650 on the upper surface 620 of the smartwatch.

In the embodiment of FIGS. 9-18, the internal battery 910 of the smartwatch 600 is the main battery, and the removable battery pack 610 is the auxiliary battery.

FIGS. 19 and 20 illustrate an upper perspective view and a lower perspective view, respectively, of a first fitness tracker, or wearable device, 1100 attached to a band 1102. The band may also be referred to herein as the strap. The band allows a user (not shown) to secure the fitness tracker to a portion of a limb, such as the wrist or the ankle of the user. In the following description, the band referred to as a wristband 1102. The fitness tracker may be in wireless communication with a smartphone 1104 or another interactive device.

The fitness tracker 1100 has an upper portion 1110 and a lower portion 1112, which are attached to each other or which may be formed as an integrated component. The upper portion has a contoured shape as described below. The lower portion may have a conventional geometric shape such as the illustrated rectangular parallelepiped, a cylinder, or the like. The lower portion is secured to the wristband 1102. For example, the lower portion may extend through the wristband as illustrated. Alternatively, the wristband may be attached to peripheral surfaces of the wristband.

The upper portion 1110 of the fitness tracker 1100 has an upper surface 1120. The lower portion 1112 of the fitness tracker has a lower surface 1122. When the fitness tracker is secured to the limb portion of the user using the wristband 1102, the lower surface of the fitness tracker contacts the skin of the limb portion. In the illustrated embodiment, the upper surface has a contour, a texture and a color that may be selected for aesthetic reasons. Unlike conventional fitness trackers, the upper surface in the illustrated embodiment is not interactive and does display information or accept tactile inputs from the user. In alternative embodiments, the upper surface may have a display and a tactile input device while retaining the disclosed contour.

As illustrated in FIG. 20, the lower surface 1122 of the fitness tracker 1100 can include at least one sensor 1130 that interacts with the skin of the user's wrist (or ankle) to obtain physiological parameters indicative of the physical condition of the user. For example, the sensor may be a blood oxygenation sensor as illustrated in FIG. 20. The sensor may also be a heartrate sensor, a temperature sensor, a bioimpedance sensor, an electrocardiogram (ECG) sensor or other physiological parameters. Such sensors are well known in the art and are not described in detail herein. In certain embodiments the lower surface of the fitness tracker may not have an exposed sensor. For example, the fitness tracker may have internal components configured to operate as a motion tracker (e.g., a step counter). The motion tracker may also sense orientation of the user, direction of movement and the spatial position of the user (e.g., using an internal GPS). For the purpose of the description herein, the tracking of motion, orientation, location and the like is also identified as the sensing of a physiological parameter of the user.

The fitness tracker 1100 can include internal circuitry that is configured to perform a fitness-related sensing function. For example, FIG. 21 illustrates an electronic circuit 1200 that senses a physiological parameter of the user via the sensor 1130 on the lower surface 1122 of the fitness tracker. The sensor is controlled by a processor 1210 that sends commands or signals to and receives sensed information from the sensor via a sensor interface 1220. The structures and operations of various types of physiological sensors are well known and are not described herein.

The electronic circuit 1200 can further include a wireless interface 1240, such as a Bluetooth® interface or another suitable interface. The processor 1210 receives input commands and inquiries from the smartphone 1104 (FIG. 19) and sends information to the smartphone via the wireless interface. The user may use the smartphone to set up the fitness tracker and to provide information about the user to enable the processor to evaluate the sensed information from the sensor 1130. In the illustrated embodiment, the fitness tracker can include an alert device 1250 (e.g., a piezoelectric vibrator or the like) that can be activated by the processor to inform the user that an event has occurred. The user can then use an application on the smartphone to access the information within the fitness tracker to determine the cause of the alert.

The electronic circuit 1200 can further include an internal battery 1260 that provides electrical power to the processor 1210, the sensor interface 1220 and wireless interface 1240 via a voltage generator 1262. The battery can be recharged via a charging antenna 1264 within the fitness tracker 1100 by placing the fitness tracker on a magnetic induction charger (not shown) or connecting the fitness tracker to a source (not shown) of DC electrical energy.

In some cases, only one of two or more fitness trackers (e.g., fitness tracker 1100 and fitness tracker 1330) includes a processor 1210. For example, the fitness tracker 1100 can include a sensor for sensing a first physiological parameter of a user and a processor for receiving and processing the sensed information from the sensor. The fitness tracker 1300 can include a sensor for sensing a second physiological parameter of a user different than the first physiological parameter. Instead of including a processor like the fitness tracker 1100 for receiving and processing the sensed information from the sensor, the fitness tracker 1300 can wirelessly transmit the sensed information from the sensor to the fitness tracker 1100 and/or the smartphone 1104 using the wireless interface. The wireless interface of fitness tracker 1100 can receive the sensed information from the fitness tracker 1300 and transmit it to the processor. The processor of the fitness tracker 1100 can receive and process the sensed information from the fitness tracker 1300. After receiving and processing the sensed information from the fitness trackers 1100, 1300 the wireless interface of the fitness tracker 1100 can send the processed sensed information to the smartphone 1104. In some cases, the smartphone 1104 can provide a visual representation of the sensed information of fitness trackers 1100, 1300. In some cases, none of the fitness trackers include a processor or the processor is not configured to process the sensed information from the fitness trackers. In such cases, the sensed information from the fitness trackers is transmitted to the smartphone 1104 where a processor of the smartphone 1104 can receive and process the sensed information from the fitness trackers 1100, 1300. The smartphone 1104 can provide a visual representation of the sensed information from the fitness trackers 1100, 1300.

In certain embodiments, the lower surface 1122 of the fitness tracker 1100 may not have a sensor. For example, FIG. 22 illustrates an electronic circuit 1270 that operates as a step counter or other motion tracking device. The fitness tracker can include an internal motion sensor 1280 that senses the orientation and motion of the user. The motion sensor may be used, for example, to determine the physical activity of the user. Motion sensors are well known in the fitness tracking art and are not described in detail herein.

As described herein, each fitness tracker 1100 has a dedicated purpose and does not include features that the user does not want or need. As discussed above, one embodiment of the fitness tracker can be configured with an internal motion sensor to count steps and other activities. Another embodiment of the fitness tracker can be configured as an optical sensor. Still another embodiment of the fitness tracker can be configured as a temperature sensor. Still another embodiment of the fitness tracker can be configured as an electrical sensor. Other embodiments of the fitness tracker can be configured with other fitness tracking features. A user wanting only one feature can purchase a fitness tracker having the desired feature without paying the additional costs for unwanted features. A user wanting an additional feature can purchase an additional fitness tracker having the additional feature. In some cases, each fitness tracker 1100 does not include more than one sensor.

As discussed above, by providing embodiments of the fitness tracker 1100 with each embodiment having only a single feature, a user only needs to purchase an embodiment of the fitness tracker having a desired feature. A user may add a second feature by purchasing another embodiment of the fitness tracker having the second feature. For example, a user may purchase a first fitness tracker 1100 the blood oxygenation sensor 1130 and the electronics circuit 1200 of FIG. 21 and may also purchase a second fitness tracker 1300 (FIGS. 23 and 24) having the motion sensor electronic circuit 1270 of FIG. 22. Rather than having to wear two visually independent fitness trackers, the contours of the upper portion 1110 of the fitness tracker disclosed herein allows the user to wear the two fitness trackers as a single interlocked unit that has a visual appearance of a single fitness tracker. As shown in FIGS. 23 and 24, the second fitness tracker 1300 is rotated 180 degrees with respect to the first fitness tracker 1100. When the second fitness tracker is positioned adjacent to the first fitness tracker as shown in FIGS. 25 and 26, the upper portions of the two fitness trackers interlock, and the two fitness trackers have the appearance of a single device. Beneficially, the interlocking of two or more fitness trackers (e.g., fitness tracker 1100 and fitness tracker 1300) can reduce the amount of space that the fitness trackers occupy on, for example, the wrist of a user. This can allow a user to wear more fitness trackers than would otherwise be possible to wear on, for example, a wrist if the fitness trackers did not interlock with each other.

The interlocking of the upper portions 1110 of the fitness tracker 1100 and the fitness tracker 1300 illustrated in FIGS. 25 and 26 is enabled by selecting the contours of the upper portion of the fitness tracker to have symmetry along at least one plane as shown in the top plan view of FIG. 24. As shown in FIG. 24, the upper surface 1120 of the upper portion of each fitness tracker has a first side 1400 a second side 1402, a third side 1404 and a fourth side 1406.

The first side 1400 and the second side 1402 have selected contours. In the illustrated embodiment, the first side has a single smooth outwardly projecting (convex) arcuate contour 1410. The second side has a first contour 1420, which is convex in the illustrated embodiment, and has a second contour 1422, which is concave in the illustrated embodiment. The third side 1404 interconnects the upper ends of the first side and the second side and may have an arcuate contour as shown. The fourth side 1406 interconnects the lower ends of the first side and the second side and may have an arcuate contour as shown.

The curvatures (e.g., the radiuses and the arcuate lengths) of the first (convex) contour 1420 and the second (concave) contour 1422 of the second side 1402 of the upper surface 1120 of the upper portion 1110 of the fitness tracker 1100 are selected to be substantially the same. In the illustrated embodiment, the first and second contours are disposed equidistantly from a horizontal plane 1424, wherein "horizontal" is defined for the view in FIG. 25, with the first (concave) contour positioned above the horizontal plane and with the second (convex) contour positioned below the horizontal plane.

As shown in FIGS. 23 and 24, the upper portion 1110 of the second fitness tracker 1300 is identical to the upper portion 1110 of the first fitness tracker 1100. Thus, the second fitness tracker can be rotated 180 degrees with respect to the first fitness tracker such that the first fitness tracker and the second fitness tracker can be positioned adjacent to each other as shown in FIGS. 25 and 26. When positioned as shown in FIGS. 25 and 26, the first (convex) contour 1420 of the second fitness tracker engages the second (concave) contour 1422 of the second fitness tracker. The second (convex) contour of the second fitness tracker engages the first (concave) contour of the first fitness tracker. The resulting pair of adjacent upper surfaces 1120 of the two fitness trackers has the appearance of a single upper surface. When interlocked as shown in FIGS. 25 and 26, portions of the first fitness tracker 1100 and the second fitness tracker 1300 can contact one another along an abutment juncture having a serpentine shape.

When attached to the limb of a user, the two adjacent fitness trackers 1100, 1300 communicate with the smartphone 1104 independently as illustrated in FIG. 25.

As further illustrated in FIG. 23, the wristband 1102 of each fitness tracker 1100, 1300 can include a plurality of optional embedded magnets which are positioned to engage each when the two wristbands are adjacent. For example, a first magnet 1430 may have an exposed N pole and a second magnet 1432 may have an exposed S pole. When the two fitness trackers are aligned as shown in FIG. 24, the poles of opposite polarity are aligned and hold the wristbands together. The force of the magnets is selected to be sufficient to hold the wristbands together; however, the user may easily separate the magnets to separate the wristbands. The wristbands can also include a third magnet 1434 with an exposed N pole and a fourth magnet 1436 with an exposed S pole.

The illustrated first (convex) contour 1420 and the second (concave) contour 1422 are examples of contours that enable one of two fitness trackers having identical contours to be rotated with respect to the other fitness tracker such that the contours of the rotated fitness tracker engage the contours of the other fitness tracker. Other contours can also be used as long as the contour has a symmetry that allows the illustrated engagement. In further alternative embodiments, the contours of an engagement side of one fitness tracker may differ from the contours of an engagement side of another fitness tracker. For example, one fitness tracker may have an engagement surface with first and second convex contours with a concave contour interposed between the two convex contours. A second fitness tracker may have an engagement surface with first and second concave contours with a convex contour interposed between the two concave contours. When the two fitness trackers are engaged, the two convex contours of the first fitness tracker engage the two convex contours of the second fitness tracker, and the concave contour of the first fitness tracker engages the convex contour of the second fitness tracker.

If a user wants to add a third feature to the first and second features described above, the user can purchase a third fitness tracker 1500 with the desired third feature. The third fitness tracker is illustrated in FIGS. 27 and 28. Unlike the first fitness tracker 1100 and the second fitness tracker 1300, the third fitness tracker 1500 has a modified shape that enables the third fitness tracker to fit between and interlock with the first fitness tracker and the second fitness tracker. The third fitness tracker is mounted on or attached to a wristband 1502 as described above.

The third fitness tracker 1500 has an upper portion 1510 and a lower portion (not shown). The lower portion of the third fitness tracker extends through the wristband as previously described. The upper portion of the third fitness tracker has an upper surface 1520, which has a first (left) side 1530, a second (right) side 1532, a third (upper) side 1534, and a fourth (lower) side 1536.

The second side 1532 of the upper surface 1520 of the upper portion 1510 of the third tracker 1500 has a first contour 1540, which is convex in the illustrated embodiment, and has a second contour 1542, which is concave in the illustrated embodiment. The first (convex) contour and the second (concave) contour of the second side of the upper surface of the third fitness tracker correspond in radius, arcuate length and position to the first (convex) contour 1420 and the second (concave) contour 1422 of the upper surface 1120 of the upper portion 1110 of the first fitness tracker 1100. The first and second contours are disposed equidistantly from a horizontal plane 1544, with the first (concave) contour positioned above the horizontal plane and with the second (convex) contour positioned below the horizontal plane as described above with respect to the first fitness tracker 1100.

Unlike the first side 1400 of the upper surface 1120 of the upper portion 1110 of the first fitness tracker 1100, the first side 1530 of the upper surface 1520 of the upper portion 1510 of the second fitness tracker has a third (concave) contour 1550 positioned above the horizontal plane 1544 and has a fourth (convex) contour 1552 positioned above the horizontal plane. The third contour and the fourth contour have radiuses and arcuate lengths corresponding to the radiuses and arcuate lengths of the first contour and the second contour.

As illustrated in FIG. 28, the third side 1534 interconnects the upper ends of the first side 1530 and the second side 1532 and may have an arcuate contour as shown. The fourth side 1536 interconnects the lower ends of the first side and the second side and may have an arcuate contour as shown.

When the third fitness tracker 1500 is positioned on the wrist of a user between the first fitness tracker 1100 and the second fitness tracker 1300 as illustrated in FIGS. 29 and 30, the upper portion 1510 of the third fitness tracker interlocks with the upper portions 1110 of the first fitness tracker and the second fitness tracker. The third (concave) contour 1550 of the third fitness tracker is aligned with and interlocks with the first (convex) contour 1420 of the first fitness tracker.

The fourth (convex) contour 1552 of the third fitness is aligned with and interlocks with the second (concave) contour 1422 of the first fitness tracker. The first (convex) contour 1540 of the third fitness tracker is aligned with and interlocks with the second (concave) contour 1422 of the second fitness tracker. The second (concave) contour 1542 of the third fitness tracker is aligned with and interlocks with the first (convex) contour 1420 of the second fitness tracker.

It should be understood that the third fitness tracker 1500 is rotationally symmetrical about an axis 1560 (FIG. 27), which is perpendicular to the upper surface 1520 and which is centered on the upper surface. This symmetry enables the third fitness tracker to be rotated 1180 degrees such that the first (convex) contour 1540 of the third fitness tracker engages the second (concave) contour 1422 of the first fitness tracker; the second (concave) contour 1542 of the third fitness tracker engages the first (convex) contour 1420 of the first fitness tracker; the third (concave) contour 1550 of the third fitness tracker engages the first (convex) contour 1420 of second fitness tracker; and the fourth (convex) contour of the third fitness tracker engages the second (concave) contour of the second fitness tracker. The resulting interlocks of the upper portions of the fitness trackers with the third fitness tracker rotated 180 degrees would have the same visual appearance as illustrated in FIGS. 29 and 30.

Additional fitness trackers 1500 with differing sensing features can be interposed between the first fitness tracker 1100 and the second fitness tracker 1300 to expand the capabilities of the combined interlocked fitness trackers.

Two or more of the third fitness trackers 1500 can be positioned on the wrist of a user without using either the first fitness tracker 1100 or the third fitness tracker 1300. For example, FIG. 31 illustrates three interlocked third fitness trackers.

FIG. 32 illustrates an exploded upper perspective view of an embodiment of a smartwatch 2100 attached to a wristband 2102. The smartwatch has a first screen display 2110 and second screen display 2120. In FIG. 32, the second screen display is shown spaced apart from the first screen display for illustration only. FIGS. 33 and 34 illustrate the second screen display installed as an overlay over the first screen display. In FIG. 33 the second screen display is activated to represent an analog watch as described below. In FIG. 34, the second screen display is deactivated to provide visual access to the first screen display as described below.

The first screen display 2110 is an interactive screen display that displays data and graphic information in response to user commands. For example, the first screen display may be an OLED screen that directly displays the data and graphic information. The first screen display is touch sensitive such that a user can touch various icons (not shown) on the first screen display to initiate commands or to respond to information on the first screen display. For example, the first screen display may be an OLED screen that directly displays the data and graphic information.

The second screen display 2120 is an e-paper display, which may also be referred to as an e-ink display. Such displays are well-known in the art and are not described in detail herein. Basically, an e-paper display can include tiny capsules filled with charged ink particles. When a proper electrical voltage is applied to selected particles, the ink darkens to mimic the appearance of an image on paper. Once an image is formed, the image is maintained without any requirement for additional power until a change in the image is made.

The second screen display 2120 is positioned as overlay over the first interactive screen display 2110. The second screen display is electrically connected to circuitry within the smartwatch 2100. In the illustrated embodiment, commands are sent from the smartwatch to the second screen display to configure outer image portions 2122 of the display to represent the dial of an analog watch, to configure a second image portion 2124 to represent the hour hand of the watch and to configure a third image portion 2126 to represent the minute hand of the analog watch. Additional image portions (not shown) can be configured to represent images of some or all of the numerals representing the hours around the dial of the analog watch, to represent an image of the second hand of the analog watch, to represent an images of letters identifying the day of the week and alphanumeric images to represent the date.

Typically, the smartwatch 2100 only needs to communicate with the second screen display 2120 to erase and re-display the image 2126 of the minute hand and the image 2124 of the hour hand as the time changes. If day and date are displayed, the smartwatch only needs to update the images representing that information once per day. Since power is only required to erase and rewrite selected images on the second screen display, the second screen display inherently requires very little power for operation. Accordingly, the time of day is constantly available for viewing by the user while the smartwatch is in the analog watch mode. In some embodiments, the smartwatch can include a temporary backlighting mode so that the user may be able to view the images of the watch hands in low lighting conditions. In the analog watch mode of operation, the interactive screen display 2110 is deactivated, and very little power is required to operate the smartwatch.

The smartwatch 2100 can include a mode switch 2130 that a user may activate to switch the operational mode of the smartwatch from the analog watch mode describe above to an interactive display mode and to switch the smartwatch back to the analog display mode. The operation of the smartwatch in the interactive display mode is illustrated in FIG. 34.

In FIG. 34, the second screen display 2120 is effectively turned off by erasing the images representing the analog watch. Accordingly, the second screen display is illustrated as being transparent in FIG. 34. The images of the watch dial and the hands are shown in phantom in FIG. 34 to indicate that the images are not visible with the second screen display is deactivated in this operational mode.

In FIG. 34, the first screen display 2110 is turned on to display selected images in accordance with an application selected by the user. For example, FIG. 34 represents an example of the images displayed when the user operates the smartwatch as a fitness tracker. The smartwatch has one or more sensors (not shown) on a lower surface of the smartwatch that are positioned in contact with the skin of the user when the wristband 2102 is secured to the user's wrist. The first screen display displays a first numeral 2150 representing a first sensed physiological parameter of the user, displays a second numeral 2152 representing a second physiological parameter of the user and displays a third numeral 2154 representing a third physiological parameter of the user. The first screen display may also display an image 2160 of a graphical representation of a physiological parameter of the user.

Since the second screen display 2120 is transparent, the user is able to view the information displayed on the first screen display 2110. The second screen display is sufficiently thin that the user may touch the exposed surface of the second screen display to tactilely interact with the first screen display in a similar manner to interacting with a smartphone through a screen protector.

When the user completes his or her interactions with the features of the selected application of the smartwatch 2100, the user may return to the analog watch mode by engaging the mode switch 2130. Some applications of the smartwatch may be programmed to return the smartwatch to the analog watch mode when the user exits the applications.

Terminology

Conditional language used herein, such as, among others, "can," "might," "may," "for example," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain examples require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various examples, it will be understood that various omissions, substitutions, and changes in the form and details of the devices or algorithms illustrated can be made without departing from the spirit of the disclosure. As will be recognized, the inventions described herein can be embodied within a form that does not provide all of the features and benefits set forth herein, as some features can be used or practiced separately from others.

As various changes could be made in the above constructions without departing from the scope of the invention, it is intended that all the matter contained in the above description or shown in the accompanying drawings shall be interpreted as illustrative and not in a limiting sense.

What is claimed is:

1. A wearable device for monitoring one or more physiological parameters of a user, the device comprising:
   a main body configured for placement on a user's limb, the main body comprising a top surface, a display on the top surface of the main body, and a first input electrode and a second input electrode positioned on a bottom surface of the main body;
   a first battery inside the main body; and
   a removable housing comprising a second battery, a top surface, and an opening along the top surface of the removable housing, said removable housing comprising a plurality of attachment legs configured to engage the main body to removably secure the removable housing over the top surface of the main body, the removable housing including at least a first output electrode positioned on an inner surface of a first attachment leg of the plurality of attachment legs and a second output electrode positioned on an inner surface of a second attachment leg of the plurality of attachment legs, the first output electrode positioned on the first attachment leg such that the first output electrode contacts the first input electrode when the removable housing is secured to the main body and such that the second output electrode on the second attachment leg contacts the second input electrode when the removable housing is secured to the main body,
   wherein, when the removable housing is attached to the main body, the second battery of the removable housing is configured to charge the first battery within the main body via the first and second input electrodes and the first and second output electrodes; and
   wherein the opening along the top surface of the removable housing permits visualization of the display of the main body when the removable housing is attached to the main body.

2. The wearable device of claim 1, wherein the removable housing portion does not include a display.

3. The wearable device of claim 1, further comprising a band comprising a first end and a second end, wherein the first end attaches to a first end of the main body and the second end attaches to a second end of the main body.

4. The wearable device of claim 1, wherein:
   the main body further comprises a third input electrode and a fourth input electrode positioned on the bottom surface of the main body;
   the removable housing further comprises a third output electrode positioned on an inner surface of a third attachment leg of the plurality of attachment legs and a fourth output electrode positioned on an inner surface of a fourth attachment leg of the plurality of attachment legs; and
   the third output electrode contacts the third input electrode and the fourth output electrode contacts the fourth input electrode when the removable housing is secured to the main body.

5. The wearable device of claim 1, wherein the main body further comprises at least one sensor for sensing a physiological parameter of the user when the wearable device is in use.

* * * * *